United States Patent [19]

Foung et al.

[11] Patent Number: 6,110,662
[45] Date of Patent: Aug. 29, 2000

[54] HTLV-I/HTLV-II ASSAY AND METHOD

[75] Inventors: Steven K. H. Foung, Stanford; Kenneth G. Hadlock, Union City; Theresa P. Chow, Portola Valley, all of Calif.

[73] Assignees: Genelabs Technologies, Inc., Redwood City; The Board of Trustees of the Leland Stanford Junior University, Stanford, both of Calif.

[21] Appl. No.: 08/236,886

[22] Filed: Apr. 28, 1994

Related U.S. Application Data

[63] Continuation of application No. 07/840,906, Feb. 24, 1992.

[51] Int. Cl.$^7$ ...................................................... C12Q 1/70
[52] U.S. Cl. ............................... 435/5; 435/7.1; 435/810; 435/975
[58] Field of Search ................................ 435/5, 810, 975, 435/974, 7.9, 973, 7.92, 7.93, 7.94, 7.95, 7.1; 436/518

[56] References Cited

U.S. PATENT DOCUMENTS

| | | |
|---|---|---|
| 5,003,043 | 3/1991 | Akita et al. . |
| 5,017,687 | 5/1991 | Vahlne et al. . |
| 5,039,604 | 8/1991 | Papsidero et al. . |
| 5,066,579 | 11/1991 | Reyes et al. ................................ 435/5 |
| 5,108,896 | 4/1992 | Philo et al. ............................... 435/7.5 |
| 5,283,320 | 2/1994 | Vahlne et al. . |
| 5,359,029 | 10/1994 | Lacroix et al. .......................... 530/300 |

FOREIGN PATENT DOCUMENTS

| | | |
|---|---|---|
| 0267622A2 | 11/1987 | European Pat. Off. . |
| 0439077A2 | 7/1991 | European Pat. Off. . |
| 0482605A3 | 4/1992 | European Pat. Off. . |
| WO/86/01834 | 3/1986 | WIPO . |
| WO/89/08664 | 9/1989 | WIPO . |
| WO/90/08162 | 7/1990 | WIPO . |
| 9010231 | 9/1990 | WIPO . |
| WO/90/10231 | 9/1990 | WIPO . |
| 9015820 | 12/1990 | WIPO ............................... C07K 7/10 |
| WO/90/15820 | 12/1990 | WIPO . |
| WO/92/01713 | 2/1992 | WIPO . |
| WO/92/04046 | 3/1992 | WIPO . |
| WO/93/01316 | 1/1993 | WIPO . |
| WO/93/02102 | 2/1993 | WIPO . |
| WO/93/06843 | 4/1993 | WIPO . |
| WO/93/11431 | 6/1993 | WIPO . |

OTHER PUBLICATIONS

Tijssen, "Practice & Theory of Enzyme Immunoassays" Elsevier, NY, 1985. pp 11–20, 329–349.

Lillehoj et al, J. Clin. Micro 28(12):2653–58, 1990.

Gosling, Clin Chem. 36(8)1408–1427, 1990.

Horal et al., "Identification of Type–Specific Linear Peptides . . . ," Proc. Natl. Acad Sci 88:5754–5758 (1991).

Washitani et al, "Serological Discrimination between HTLV–I and HTLV–II antibodies by ELISA using Synthetic Peptides as Antigens." Int. J. Cancer 49:173–177, 1991.

Wide, L. Noncompetitive versus Competitive Binding Assays. In: Principles of Competitive Binding Assays, Odell, W. D. et al., eds., New York: John Wiley & Sons, 1983, Ch. 13, pp. 243–254.

Viscidi, R.P., et al, Diagnosis and Differentiation of HTLV–I and HTLV–II Infection by Enzyme Immunoassay Using Synthetic Peptides, J. Acquired Immune Defic. Syndromes 4: 1190–98, 1991.

Anderson, D., et al., "Licensure of Screening Tests for Antibody to Human T–Lymphotropic Virus Type I" *MMWR* 37(48):736–747 (1988).

Anderson, D.W., et al., "Serological Confirmation of Human T–Lymphotropic Virus Type I Infection in Healthy Blood and Plasma Donors" *Blood* 74(7):2585–91 (1989).

Blomberg, J., et al., "Type– and Group–Specific Continuous Antigenic Determinants of HTLV. Use of Synthetic Peptides for Serotyping of HTLV–I and –II Infection" *J. Acquired Immune Deficiency Syn.*, 5(3):294–302 (1992).

Bonis, J., et al., "Discrimination between Human T–Cell Lymphotropic Virus Type I and II (HTLV–I and HTLV–II) Infections by Using Synthetic Peptides Representing an Immunodominant Region of the Core Protein (p19) of HTLV–I and HTLV–II" *Journal of Clinical Microbiology* 31(6):1481–5 (1993).

Buckner, C., et al., "Immune Responsiveness to the Immunodominant Recombinant Envelope Epitopes of Human T Lymphotropic Virus Types I and II in Diverse Geographic Populations" *J. Infectious Dis.* 166 (Nov.):1160–3.

Gosling, J.P., "A Decade of Development in Immunoassay Methodology" *Clinical Chemistry*, 36(8):1408–27 (1990).

Hattori, S., et al., "Indetification of gag and env Gene Products of Human T–Cell Leukemia Virus (HTLV)" *Virology* 136:338–347 (1984).

Kiyokawa, T., et al., "Envelope proteins of human T–cell leukemia virus: Expression in *Escherichia coli* and its application to studies of env gene functions" *Proc. Nat. Acad. Sci. USA* 81 (Oct.).:6202–6206 (1984).

(List continued on next page.)

Primary Examiner—Yvonne Eyler
Assistant Examiner—Brenda Brumback
Attorney, Agent, or Firm—Linda R. Judge; Iota Pi Law Group

[57] ABSTRACT

Method and assay kit for positively identifying HTLV-I and HTLV-II infection from human serum samples. The kit includes peptide antigens from the C-terminal regions of HLTV-I p19 and HTLV-II p21 gag proteins, and peptide antigens from the HLTV-I and HTLV-II env proteins immobilized on a solid support. After reaction of the serum sample with the solid support, an antibody-detection reagent in the kit is added to the support, to detect binding of human serum antibodies to each of the peptide antigens separately. The test allows positive identification of HTLV-I or HTLV-II when antibody binding to each HTLV-I or HTLV-II gag and env peptide antigen, respectively, is observed. Also disclosed is a kit for screening human sera for evidence of HTLV-I or HTLV-II infection.

15 Claims, 13 Drawing Sheets

OTHER PUBLICATIONS

Kuroda, N., et al., "Detection of antibodies to Human T–Lymphotropic Virus Type I by using synthetic peptides" *Int. J. Cancer* 45:865–868 (1990).

Lal, R.B., et al., "Characterization of Immunodominant Epitopes of gag and pol Gene Encoded Proteins of Human T–Cell Lymphotropic Virus Type I" *J. Virology* 65(4):1870–1876 (1991).

Lal, R.B., et al., "Serologic Discrimination of Human T Cell Lymphotropic Virus Infection by Using a Synthetic Peptide–Based Enzyme Immunoassay" *J. Infect. Dis.* 163(Jan.):41–46 (1991).

Lillehoj, E.P., et al., "Development and Evaluation of a Human T–Cell Leukemia Virus Type I Serologic Confirmatory Assay Incoporating a Recombinant Envelope Polypeptide" *J. Clin. Microbiol.* 28(12):2653–8 (1990).

Lipka, J.J., et al., "Segregation of Human T Cell Lymphotropic Virus Type I and II Infections by Antibody Reactivity to Unique Viral Epitopes" *J. Infect. Dis.* 165(Feb.):268–272 (1992).

Manns, A., et al., "Detection of Early Human T–Cell Lymphotropic Virus Type I Antibody Patterns During Seroconversion Among Transfusion Recipients" *Blood* 77(4):896–905 (1991).

Matsushita, S., et al., "Human monoclonal antibody directed against an envelope glycoprotein of human T–cell leukemia virus type I" *Proc. Natl. Acad. Sci. USA* 83(Apr.):2672–6 (1986).

Noraz, N., et al., "Expression of HTLV ENVA and Tax Recombinant Peptides in Yeast: Identification of Immunogenic Domains" *Virology* 193:80–8 (1993).

Palker, T.J., et al., "Mapping of Immunogenic Regions of Human T Cell Leukemia Virus Type I (HTLV–I) gp46 and gp21 Envelope Glycoproteins with Env–encoded Synthetic Peptides and a Monoclonal Antibody to gp46" *J. Immunol.* 142(3):971–8 (1989).

Palker, T.J., et al., "C–Terminal Region of Human T Cell Lymphotropic Virus Type I (HTLV$_I$) p19 Core Protein is Immunogenic in Humans and Contains an HTLV$_I$–Specific Epitope" *J. Immunol.* 136(7):2393–7 (1986).

Palker, T.J., et al., "Monoclonal Antibodies Reactive With Human T Cell Lymphotropic Virus (HTLV$_I$) P19 Internal Core Protein: Cross–Reactivity With Normal Tissues and Differential Reactivity With HTLV Types I and II" *J. Immunol.* 135(1):247–254 (1985).

Ralston, S., et al., "Identification and Synthesis of the Epitope for a Human Monoclonal Antibody Which Can Neutralize Human T–cell Leukemia/Lymphotropic Virus Type I" *J. Biol. Chem.* 264(28):16343–6 (1989).

Robert–Guroff, M., et al., "Detection of the Human T Cell Lymphoma Virus p19 in Cells of Some Patients with Cutaneous T Cell Lymphoma and Leukemia Using a Monoclonal Antibody" *J. Experimental Med.* 154(Dec.):1957–64 (1981).

Roberts, B.D., et al., "Evaluation of an Immunoblot Assay for Serological Confirmation and Differentiation of Human T–Cell Lymphotropic Virus Types I and II" *J. Clin. Micro.* 31(2):260–4 (1993).

Samuel, K.P. et al., "Diagnostic Potential or Human Malignancies of Bacterially Produced HTLV–I Envelope Protein" *Science* 226(Nov.):1094–1097 (1984).

Seiki, M., et al., "Human adult T–cell leukemia virus: Complete nucleotide sequence of the provirus genome integrated in leukemia cell DNA" *Proc. Natl. Acad. Sci. USA* 80(Jun.):3618–3622 (1983).

Tijssen, P. "Practice and Theory of Enzyme Immunoassays", Published by Elsevier, N.Y., pp. 11–20 and 329–349 (1985).

Washitani, Y., et al., "Linear Antigenic Regions of the Structural Proteins of Human T–Cell Lymphotropic Virus Type I Detected by Enzyme–Linked Immunosorbent Assays Using Synthetic Peptides as Antigens" *J. Clin. Micro.* 30(2):287–90 (1992).

Williams, A.E., et al., "Human T–Lymphotropic Virus Type I Screening in Voluteer Blood Donors—United States, 1989" *MMWR* 39(50):915–24 (1990).

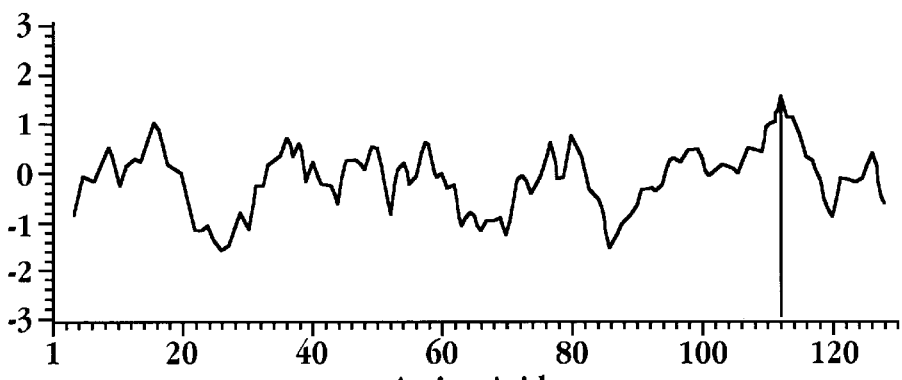
Fig. 3A
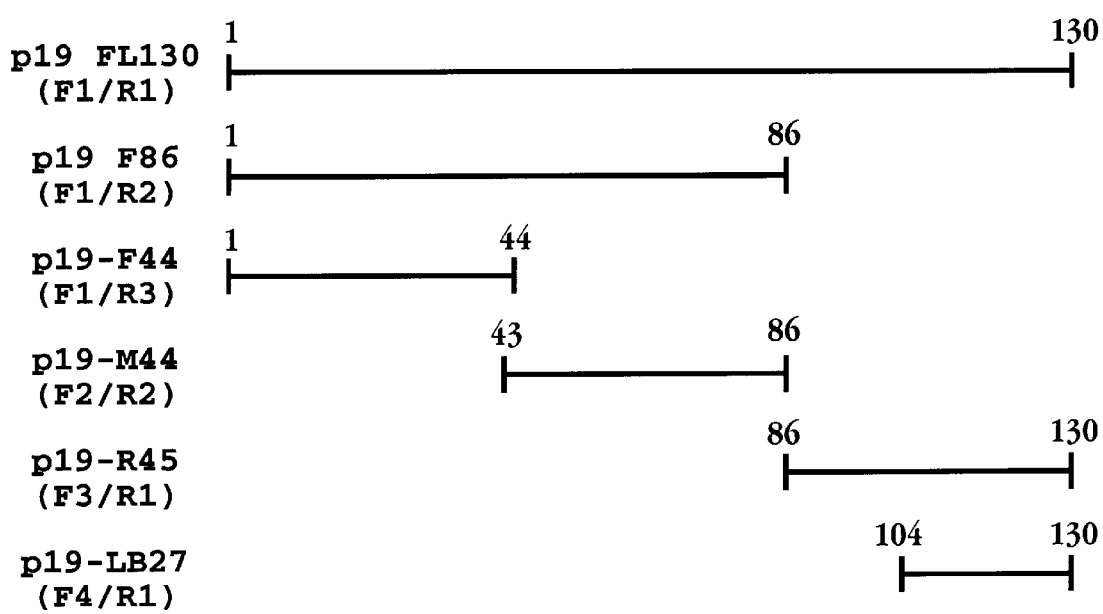
Fig. 3B
```
              *                    *                                  *
              86                   104                                130
p19-R45    ILIQTQAQIPSRPAPPPPSSPTHDPPDSDPQIPPPYVEPTAPQVL
p19-LB27                        SSPTHDPPDSDPQIPPPYVEPTAPQVL
```
Fig. 3C

```
GH1p19-F1    GC GAA TCC . ATG GGC CAA ATC TTT TCC CGT
                              *                        *
                             802                      822

GH1p19-F2    GC GAA TCC . TTC CAC CAG TTA AAG AAA TTT CTT
                              *                            *
                             928                          951

GH1p19-F3    GC GAA TCC . ATA CTC ATC CAA ACC CAA GCC
                              *                        *
                            1056                     1077

GH1p19-F4    GC GAA TCC . ACT TCC CCC ACC CAC GAC CCC
                              *                        *
                            1111                     1131
```

Reverse Primers

```
GH1p19-R1    GC GAA TCC . AAG GAC TTG GGG GGC CGT AGG
                              *                        *
                            1191                     1171

GH1p19-R2    GC GAA TCC . TAT GTG TAA AAT TTC ATT CAC
                              *                        *
                            1059                     1039

GH1p19-R3    GC GAA TCC . GTG GAA ATC GTA ACT GGA GGG
                              *                        *
                             933                      913
```

Fig. 4A

```
K55F    TTCCATGGATGCCCCTGGATATGATCC

K55R    CCGGATCCTATTATTTGGTCGTCCAGGACGT
```

Fig. 4B

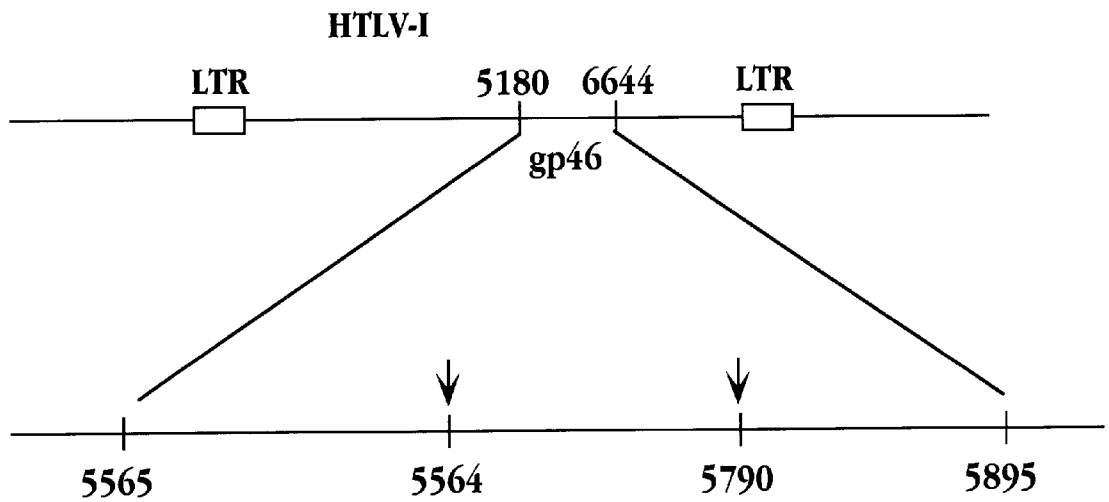

```
 gt-SLLVDAPGYDPIWFLNTEPSQLPPTAPPLLPHSNLDHILEPSIPW-gt                                gp46-MTA-1

FPFSLLVDAPGYDPIWFLNTEPSQLPPTAPPLLPHSNLDHILEPSIPWKSKLLTLVQLTLQSTNYYCIVCIDRASLSTWHVLY-  HTLV-I
||    |||||||||| ||   || | ||| |||   | | | | ||| |  | |   ||||||||| | || || ||| |||||
CGSSMTLLVDAPGYDPLWFITSEPTQPPPTSPPLVHDSDLEHVLTPSTSWTTKILKFIQLTLQSTNYSCMVCVDRSSLSSWHVLY- HTLV-II gt-MTLLVDAPGYDPLWFITSEPTQPPPTSPPLVHDSDLEHVLTPSTSWTTK-gt                            GH2-K15

DAPGYDPLWFITSEPTQPPPTSPPLVHDSDLEHVLTPSTSWTTK                               gp46-K55
```

SERUM (Ab)

DETECTION REAGENT

SERUM (Ab)

DETECTION REAGENT

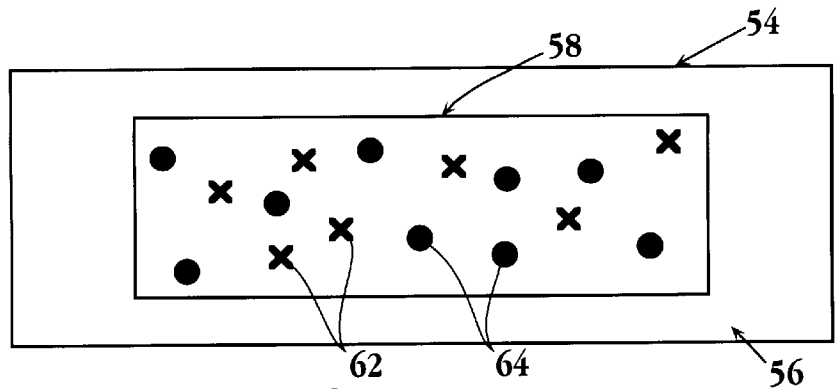
Fig. 15A
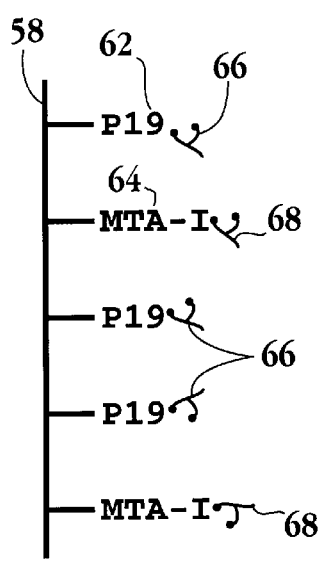
Fig. 15B
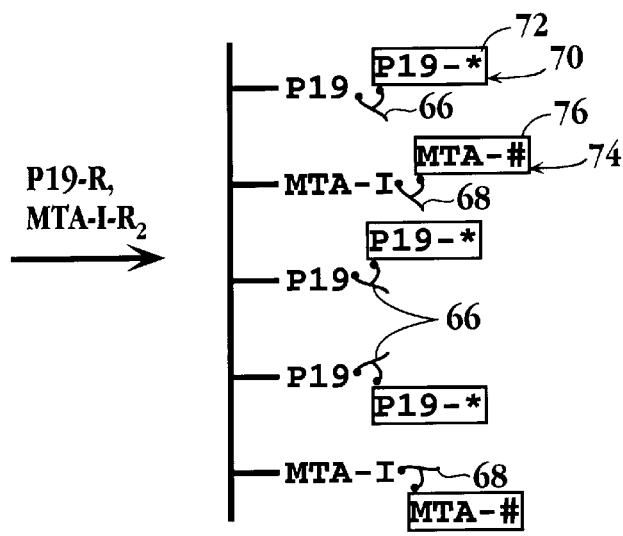
Fig. 15C
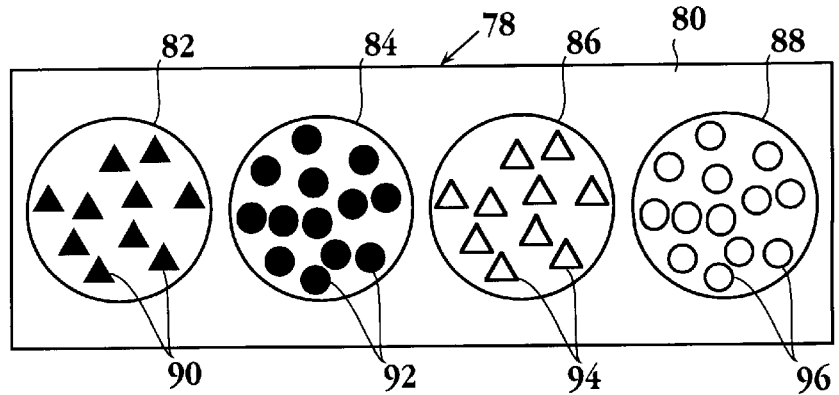
Fig. 16

SEQUENCE LISTING (1) GENERAL INFORMATION:

(iii) NUMBER OF SEQUENCES: 17

(2) INFORMATION FOR SEQ ID NO:1:

(i) SEQUENCE CHARACTERISTICS:
      (A) LENGTH: 27 amino acids
      (B) TYPE: amino acid
      (D) TOPOLOGY: linear (ii) MOLECULE TYPE: protein (iii) HYPOTHETICAL: NO (vi) ORIGINAL SOURCE:
      (C) INDIVIDUAL ISOLATE: Figure 2A, p19-C27

(xi) SEQUENCE DESCRIPTION: SEQ ID NO:1:

```
Ser Ser Pro Thr His Asp Pro Pro Asp Ser Asp Pro Gln Ile Pro Pro
1               5                  10                  15

Pro Tyr Val Glu Pro Thr Ala Pro Gln Val Leu
            20                  25
```

(2) INFORMATION FOR SEQ ID NO:2:

(i) SEQUENCE CHARACTERISTICS:
      (A) LENGTH: 45 amino acids
      (B) TYPE: amino acid
      (D) TOPOLOGY: linear (ii) MOLECULE TYPE: protein (iii) HYPOTHETICAL: NO (vi) ORIGINAL SOURCE:
      (C) INDIVIDUAL ISOLATE: Figure 3, p19-R45, p19-C45

(xi) SEQUENCE DESCRIPTION: SEQ ID NO:2:

```
Ile Leu Ile Gln Thr Gln Ala Gln Ile Pro Ser Arg Pro Ala Pro Pro
1               5                  10                  15

Pro Pro Ser Ser Pro Thr His Asp Pro Pro Asp Ser Asp Pro Gln Ile
            20                  25                  30

Pro Pro Pro Tyr Val Glu Pro Thr Ala Pro Gln Val Leu
        35                  40                  45
```

(2) INFORMATION FOR SEQ ID NO:3:

(i) SEQUENCE CHARACTERISTICS:
      (A) LENGTH: 27 amino acids
      (B) TYPE: amino acid
      (D) TOPOLOGY: linear (ii) MOLECULE TYPE: protein (iii) HYPOTHETICAL: NO (vi) ORIGINAL SOURCE:
      (C) INDIVIDUAL ISOLATE: Figure 2B, p21-C27

(xi) SEQUENCE DESCRIPTION: SEQ ID NO:3:

```
Thr Pro Pro Pro Pro Pro Pro Ser Pro Glu Ala His Val Pro Pro
1               5                  10                  15

Pro Tyr Val Glu Pro Thr Thr Thr Gln Cys Phe
            20                  25
```

```
(2) INFORMATION FOR SEQ ID NO:4:

(i) SEQUENCE CHARACTERISTICS:
        (A) LENGTH: 48 amino acids
        (B) TYPE: amino acid
        (D) TOPOLOGY: linear (ii) MOLECULE TYPE: protein (iii) HYPOTHETICAL: NO (vi) ORIGINAL SOURCE:
        (C) INDIVIDUAL ISOLATE: Figure 2C, gp46-MTA-1

(xi) SEQUENCE DESCRIPTION: SEQ ID NO:4:

Ser Leu Leu Val Asp Ala Pro Gly Tyr Asp Pro Ile Trp Phe Leu Asn
1               5                  10                  15

Thr Glu Pro Ser Gln Leu Pro Pro Thr Ala Pro Pro Leu Leu Pro His
            20                  25                  30

Ser Asn Leu Asp His Ile Leu Glu Pro Ser Ile Pro Trp Lys Ser Lys
        35                  40                  45

(2) INFORMATION FOR SEQ ID NO:5:

(i) SEQUENCE CHARACTERISTICS:
        (A) LENGTH: 44 amino acids
        (B) TYPE: amino acid
        (D) TOPOLOGY: linear (ii) MOLECULE TYPE: protein (iii) HYPOTHETICAL: NO (vi) ORIGINAL SOURCE:
        (C) INDIVIDUAL ISOLATE: Figure 2C, gp46-K55

(xi) SEQUENCE DESCRIPTION: SEQ ID NO:5:

Asp Ala Pro Gly Tyr Asp Pro Leu Trp Phe Ile Thr Ser Glu Pro Thr
1               5                  10                  15

Gln Pro Pro Thr Ser Pro Pro Leu Val His Asp Ser Asp Leu Glu
            20                  25                  30

His Val Leu Thr Pro Ser Thr Ser Trp Thr Thr Lys
        35                  40

(2) INFORMATION FOR SEQ ID NO:6:

(i) SEQUENCE CHARACTERISTICS:
        (A) LENGTH: 49 amino acids
        (B) TYPE: amino acid
        (D) TOPOLOGY: linear (ii) MOLECULE TYPE: protein (iii) HYPOTHETICAL: NO (vi) ORIGINAL SOURCE:
        (C) INDIVIDUAL ISOLATE: Figure 12, GH2-K15

(xi) SEQUENCE DESCRIPTION: SEQ ID NO:6:

Met Thr Leu Leu Val Asp Ala Pro Gly Tyr Asp Pro Leu Trp Phe Ile
1               5                  10                  15

Thr Ser Glu Pro Thr Gln Pro Pro Thr Ser Pro Pro Leu Val His
            20                  25                  30

Asp Ser Asp Leu Glu His Val Leu Thr Pro Ser Thr Ser Trp Thr Thr
        35                  40                  45

Lys
```

(2) INFORMATION FOR SEQ ID NO:7:

(i) SEQUENCE CHARACTERISTICS:
        (A) LENGTH: 85 amino acids
        (B) TYPE: amino acid
        (D) TOPOLOGY: linear (ii) MOLECULE TYPE: protein (iii) HYPOTHETICAL: NO (vi) ORIGINAL SOURCE:
        (C) INDIVIDUAL ISOLATE: Figure 12, HTLV-I gp46

(xi) SEQUENCE DESCRIPTION: SEQ ID NO:7:

```
Cys Gly Phe Pro Phe Ser Leu Leu Val Asp Ala Pro Gly Tyr Asp Pro
1               5                   10                  15

Ile Trp Phe Leu Asn Thr Glu Pro Ser Gln Leu Pro Pro Thr Ala Pro
                20                  25                  30

Pro Leu Leu Pro His Ser Asn Leu Asp His Ile Leu Glu Pro Ser Ile
            35                  40                  45

Pro Trp Lys Ser Lys Leu Leu Thr Leu Val Gln Leu Thr Leu Gln Ser
        50                  55                  60

Thr Asn Tyr Tyr Cys Ile Val Cys Ile Asp Arg Ala Ser Leu Ser Thr
65                  70                  75                  80

Trp His Val Leu Tyr
                85
```

(2) INFORMATION FOR SEQ ID NO:8:

(i) SEQUENCE CHARACTERISTICS:
        (A) LENGTH: 85 amino acids
        (B) TYPE: amino acid
        (D) TOPOLOGY: linear (ii) MOLECULE TYPE: protein (iii) HYPOTHETICAL: NO (vi) ORIGINAL SOURCE:
        (C) INDIVIDUAL ISOLATE: Figure 12, HTLV-II gp46

(xi) SEQUENCE DESCRIPTION: SEQ ID NO:8:

```
Cys Gly Ser Ser Met Thr Leu Leu Val Asp Ala Pro Gly Tyr Asp Pro
1               5                   10                  15

Leu Trp Phe Ile Thr Ser Glu Pro Thr Gln Pro Pro Pro Thr Ser Pro
                20                  25                  30

Pro Leu Val His Asp Ser Asp Leu Glu His Val Leu Thr Pro Ser Thr
            35                  40                  45

Ser Trp Thr Thr Lys Ile Leu Lys Phe Ile Gln Leu Thr Leu Gln Ser
        50                  55                  60

Thr Asn Tyr Ser Cys Met Val Cys Val Asp Arg Ser Ser Leu Ser Ser
65                  70                  75                  80

Trp His Val Leu Tyr
                85
```

(2) INFORMATION FOR SEQ ID NO:9:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (vi) ORIGINAL SOURCE:
             (C) INDIVIDUAL ISOLATE: Figure 4, GH1p19-F1

(xi) SEQUENCE DESCRIPTION: SEQ ID NO:9:

GCGAATTCAT GGGCCAAATC TTTTCCCGT                                               29

(2) INFORMATION FOR SEQ ID NO:10:

(i) SEQUENCE CHARACTERISTICS:
             (A) LENGTH: 32 base pairs
             (B) TYPE: nucleic acid
             (C) STRANDEDNESS: single
             (D) TOPOLOGY: linear (ii) MOLECULE TYPE: DNA (genomic)

(iii) HYPOTHETICAL: NO (vi) ORIGINAL SOURCE:
             (C) INDIVIDUAL ISOLATE: Figure 4, GH1p19-F2

(xi) SEQUENCE DESCRIPTION: SEQ ID NO:10:

GCGAATTCTT CCACCAGTTA AAGAAATTTC TT                                           32

(2) INFORMATION FOR SEQ ID NO:11:

(i) SEQUENCE CHARACTERISTICS:
             (A) LENGTH: 29 base pairs
             (B) TYPE: nucleic acid
             (C) STRANDEDNESS: single
             (D) TOPOLOGY: linear (ii) MOLECULE TYPE: DNA (genomic)

(iii) HYPOTHETICAL: NO (vi) ORIGINAL SOURCE:
             (C) INDIVIDUAL ISOLATE: Figure 4, GH1p-F3

(xi) SEQUENCE DESCRIPTION: SEQ ID NO:11:

GCGAATTCAT ACTCATCCAA ACCCAAGCC                                               29

(2) INFORMATION FOR SEQ ID NO:12:

(i) SEQUENCE CHARACTERISTICS:
             (A) LENGTH: 29 base pairs
             (B) TYPE: nucleic acid
             (C) STRANDEDNESS: single
             (D) TOPOLOGY: linear (ii) MOLECULE TYPE: DNA (genomic)

(iii) HYPOTHETICAL: NO (vi) ORIGINAL SOURCE:
             (C) INDIVIDUAL ISOLATE: Figure 4, GH1p-F4

(xi) SEQUENCE DESCRIPTION: SEQ ID NO:12:

GCGAATTCTC ATCCCCCACC CACGACCCC                                               29

(2) INFORMATION FOR SEQ ID NO:13:

(i) SEQUENCE CHARACTERISTICS:
             (A) LENGTH: 29 base pairs
             (B) TYPE: nucleic acid
             (C) STRANDEDNESS: single
             (D) TOPOLOGY: linear (ii) MOLECULE TYPE: DNA (genomic)

(iii) HYPOTHETICAL: NO (vi) ORIGINAL SOURCE:
        (C) INDIVIDUAL ISOLATE: Figure 4, GH1p-R1

(xi) SEQUENCE DESCRIPTION: SEQ ID NO:13:

GCGAATTCAA GGACTTGGGG GGCCGTAGG                                              29

(2) INFORMATION FOR SEQ ID NO:14:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (vi) ORIGINAL SOURCE:
        (C) INDIVIDUAL ISOLATE: Figure 4, GH1p19-R2

(xi) SEQUENCE DESCRIPTION: SEQ ID NO:14:

GCGAATTCTA TGTGTAAAAT TTCATTCAC                                              29

(2) INFORMATION FOR SEQ ID NO:15:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (vi) ORIGINAL SOURCE:
        (C) INDIVIDUAL ISOLATE: Figure 4, GH1p19-R3

(xi) SEQUENCE DESCRIPTION: SEQ ID NO:15:

GCGAATTCGT GGAAATCGTA ACTGGAGGG                                              29

(2) INFORMATION FOR SEQ ID NO:16:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (vi) ORIGINAL SOURCE:
        (C) INDIVIDUAL ISOLATE: Figure 4, gp46-K55 peptide antigen
            K55-1

(xi) SEQUENCE DESCRIPTION: SEQ ID NO:16:

TTCCATGGAT GCCCCTGGAT ATGATCC                                                27

(2) INFORMATION FOR SEQ ID NO:17:

(i) SEQUENCE CHARACTERISTICS:
        (A) LENGTH: 31 base pairs
        (B) TYPE: nucleic acid
        (C) STRANDEDNESS: single
        (D) TOPOLOGY: linear

```
    (ii) MOLECULE TYPE: DNA (genomic)

(iii) HYPOTHETICAL: NO (vi) ORIGINAL SOURCE:
         (C) INDIVIDUAL ISOLATE: Figure 4, K55-2

(xi) SEQUENCE DESCRIPTION: SEQ ID NO:17:

CCGGATCCTA TTATTTGGTC GTCCAGGACG T                                         31
```

HTLV-I/HTLV-II ASSAY AND METHOD

This is a continuation of application Ser. No. 07/840,906, filed Feb. 24, 1992, herein incorporated by reference.

1. FIELD OF THE INVENTION

The present invention relates to antibodies and peptide antigens useful in the detection of and discrimination between HTLV-I and HTLV-II infections. The invention also relates to methods of prophylaxis and treatment of HTLV-I and HTLV-II infections.

2. REFERENCES

Boyum, A. (1968) Scand. J. Clin. Lab. Invest (Suppl.) 2197: 51.
Cann, A. J., et al. (1990), in B. N. Fields (ed.), Virology, Second edition, New York, N.Y., Raven Press Ltd, 1990, p 1501
Carroll, W. P., Thielemans, K., Dilley, J., and Levy, R. (1986) J. Immunol. Methods 89: 61.
Chen, I. S. Y, McLauglin, J., Gasson, J. C., Clark, S. C., Golde, D. W. (1983) Nature 305: 502–505.
Cwirla, S. E. et al., Proc. Natl. Acad. Sci. USA 87: 6378–6382 (1990).
Foung, S. K. H., et al., (1989), *J Immunol Methods*, 116:117.
Harlow, E., Lane, D. (1988) *Antibodies: a Laboratory Manual,* Cold Spring Harbor Laboratory, Cold Spring Harbor, N.Y.
Lal, R. B., et al., (1991), J. Virol. 65:1870.
Lillehoj, E. P., et al., (1990), *J. Clin. Microbiol.* 28:2653.
Lipka, J. J., et al., (1990), *J Infect Dis* 162:353.
Lipka, J. J., et al., (1991), *J Infect Dis.* 164:400.
Lipka, J. J., et al., (1991), *Vox Sang,* 61: 171.
Manns, A., et al., (1991), *Blood* 77:896.
Matsushita, S., et al. (1986), *Proc. Natl. Acad. Sci. USA.* 83:2672.
Messing, J. (1979), *Recomb. DNA Tech Bull.* 2:43
Mishell, B. B. and Shiigi, S. M., eds. (1980) *Selected Methods in Cellular Immunology,* W. H. Freeman and Co., San Francisco.
Miyoshi, I, et al., *Nature,* 294:770 (1981).
Palker T. J., et al., (1985) *J. Immunol.* 135:247.
Palker T. J., et al., (1986), *J. Immunol.* 136:2393.
Perkins, S. et al (1989) in Borrebaeck, C. A. K., Hagen, I. (eds) *Electromanipulation in Hybridoma Technology, A Laboratory Manual,* Stockton Press, New York.
Perkins, S., Zimmerman, U., Foung, S. K. H. (1991) Hum. Antibod. Hybridomas 2: 155–159.
Sambrook, J., et al., Molecular cloning: A laboratory manual. Cold Spring Harbor Laboratory Press. Cold Spring Harbor, N.Y.
Saxon, A. et al. (1976) *J. Immunol. Methods,* 12: 85.
Scott, J. K. et al. (1990) *Science* 249: 386–390.
Seiki, M., et al., (1983), *Proc. Natl. Acad. Sci. USA.* 80:3618.
Smith, D. B., et al., (1988), *Gene,* 67:31.
Williams, A. E. et al., (1990) *MMWR* 39: 915.

3. BACKGROUND OF THE INVENTION

The human T-cell leukemia viruses (HTLV) represent a family of T-cell retroviruses with three known members. HTLV type I (HTLV-I) has transforming activity in vitro and is etiologically linked to adult T-cell leukemia, which is known to be endemic in several parts of the world. HTLV-II is another retrovirus having transforming capacity in vitro, and has been isolated from a patient with a T-cell variant of hairy cell leukemia. HTLV-III, which has also been called lymphadenopathy-associated virus and is now known as the human immunodeficiency virus (HIV), is lytic for certain kinds of T cells and has been linked to the etiology of acquired immunodeficiency syndrome (AIDS). Unlike the HTLV-I and -II viruses, HTLV-III is not known to have in vitro transforming activity.

The diagnosis of HTLV-I infection is usually based on serum antibody response to HTLV-I peptide antigens. This usually involves an initial screening assay to identify HTLV-I antibodies, based on an enzyme immunoassay (EIA) with HTLV-I virion peptides. The assays presently used for blood screening detect about 0.5 to 0.05% HTLV-I and HTLV-II positives; of these, about 4 out of 5 are false positives. Therefore, positive sera must be further tested in a confirmatory assay, using Western blot or radioimmunoprecipitation assays which detect antibody reaction to specific HTLV-I peptide antigens.

Current blood testing procedures require confirmation tests based on immunoreaction with HTLV-I p24 gag protein and at least one of the envelop proteins gp46, gp21, or gp68. When the test antigens are prepared from virion proteins, only gp46 gives a high rate of antibody reaction with true HTLV-I seropositives. Even then, the reaction with gp46 may be detected only by additional antigen testing with a more sensitive radioimmunoprecipitation assay. The above screening and confirmation testing identifies HTLV-I and HTLV-II positives, but does not distinguish between the two HTLV viruses. Currently unequivocal differentiation between HTLV-I and HTLV-II infection can only be made by isolating the virus, followed by Southern blot analysis or selective viral nucleic acid amplification by polymerase chain reaction (PCR); however, due to the low level of infected lymphocytes in HTLV-infected individuals, not all HTLV seropositive samples will test positive when analyzed by PCR (Williams). In addition, these techniques are not suited to high volume screening of sera in the clinical setting.

It would therefore be desirable to provide an improved method for detecting and differentiating HTLV-I and HTLV-II positive sera. In particular, the improved test should be capable of detecting all HTLV-I and HTLV-II positive sera, with a minimum number of false positives, and also be able to distinguish HTLV-I from HTLV-II positive sera.

4. SUMMARY OF THE INVENTION

One aspect of the invention is an assay kit for use in positively identifying HTLV-I infection in a human patient from a serum sample. The kit includes a solid support on which are immobilized (a) an HTLV-I p19-C27 peptide antigen containing the epitope formed by the amino acid sequence SEQ ID NO: 1, and (b) an HTLV-I gp46-MTA-1 peptide antigen containing the epitope formed by the amino acid sequence SEQ ID NO: 4. Also included in the kit is a detection reagent for detecting the presence of human antibodies bound immunospecifically to each of the immobilized peptide antigens.

In one general embodiment, the two HTLV-I peptide antigens are immobilized on separate regions of a solid support.

Also in one general embodiment, the detection reagent includes HTLV-I p19 and HTLV-I gp46 peptide antigens which contain the epitopes formed by the amino acid sequences SEQ ID NOS: 1 and 4, respectively, where each antigen is labeled with a detectable reporter. Where the two peptides in the detection system are labeled with distinguishable reporters, the immobilized peptide antigens may be carried on a common region of the solid support.

The kit may also be designed for positive identification of HTLV-II. In this embodiment, the solid support further has immobilized thereon, (c) an HTLV-II p21-C27 peptide antigen containing the epitope formed by the amino acid sequence SEQ ID NO: 3, and (d) an HTLV-II gp46-K55 peptide antigen containing the epitope formed by the amino acid sequence SEQ ID NO: 5. The detecting means in this embodiment is effective for detecting the presence of human antibodies bound immunospecifically to each of the peptide antigens (a)–(d) immobilized on the solid support.

In a related aspect, the invention includes a method for positively identifying HTLV-I infection in a human patient from a serum sample. The method includes reacting the serum sample with the above solid support, and detecting the binding of human serum antibodies to each of the peptide antigens separately. From the binding pattern, the positive identification of HTLV-I or HTLV-II infection can be made if and only if binding of serum antibodies to both HTLV-I gag and env, or HTLV-II gag and env peptide antigens, respectively is made.

In another aspect the invention includes a kit for positively identifying the HTLV-II infection in a human patient from a serum sample. The kit includes a solid support on which are immobilized (a) an HTLV-II p21-C27 peptide antigen containing the epitope formed by the amino acid sequence SEQ ID NO: 3, and (b) an HTLV-II gp46-K55 peptide antigen containing the epitope formed by the amino acid sequence SEQ ID NO: 5. The kit also includes a detecting reagent effective for detecting the presence of human antibodies bound immunospecifically to each of the peptide antigens immobilized on the solid support.

In still another aspect, the invention includes a kit for screening human sera for evidence of HTLV-I or HTLV-II infection. The kit includes a solid support on which are immobilized:

(a) a peptide antigen derived from the HTLV-I gag protein p24 and defining a epitope which is immunorective with human monoclonal antibody WA10/3E4 or monoclonal antibody WA07/2G3 or a peptide antigen derived from the HTLV-I env protein gp21 and defining an epitope which is immunoreactive with the human monoclonal antibody WA07/1E4; and one of the following pairs of peptide antigens:

(b) an HTLV-I p19-C27 peptide antigen containing the epitope formed by the amino acid sequence SEQ ID NO: 1, and an HTLV-II p21-C27 peptide antigen containing the epitope formed by the amino acid sequence SEQ ID NO: 3, or (c) an HTLV-I gp46-MTA-1 peptide antigen containing the epitope formed by the amino acid sequence SEQ ID NO: 4, and an HTLV-II gp46-K55 peptide antigen containing the epitope formed by the amino acid sequence SEQ ID NO: 5.

The invention also contemplates a method and composition for HTLV-I prophylaxis. The composition for HTLV-I prophylaxis includes one of the following human monoclonal antibodies whose binding to infected cells is consistent with neutralizing antibody activity:

(a) WA07/2F7, WA08/2E9, WA07,2G3, WA11/2E2, WA04/2B10, WA07/1G7, WA07/2D3, Wa07/2F9, WA11/1F5, and WA11/2F3.

Also contemplated in the invention is a peptide vaccine composition for use in immunizing a human against HTLV-I or HTLV-II infection. The vaccine is composed of an HTLV-I or HTLV-II peptide which is immunoreactive with one of above anti-HTLV-I neutralizing antibodies. A peptide antigen is carried in a suitable adjuvant and/or derivatized to a carrier immune-potentiating carrier protein.

A related aspect of the invention includes a method of preventing or treating HTLV-I infection in an individual, by administering, e.g., by intramuscular injection, the above vaccine composition.

These and other objects and features of the invention will become more fully apparent when the following detailed description of the invention is read in conjunction with the accompanying drawings.

BRIEF DESCRIPTION OF THE FIGURES

FIGS. 3A–3C show a hydrophilicity plot of the HTLV-I gag protein p19 (A), the regions of the p19 used to produce fusion-protein antigens (3B), and sequences of the p19 regions of two of these antigens, p19-R45 (p19-C45; SEQ ID NO: 2) and p19-LB27 (p19-C27; SEQ ID NO: 1) (3C);

FIG. 4 shows oligonucleotide primers GH1p19-F1 (SEQ ID NO: 9), GHIP19-F2 (SEQ ID NO: 10), GH1P19-F3 (SEQ ID NO: 11), GHIP19-F4 (SEQ ID NO: 12), GH1P-R1 (SEQ ID NO: 13), GH1P91-R2 (SEQ ID NO. 14), and GH1P19-R3 (SEQ ID NO: 15) used in producing fusion peptide coding sequences of p21 peptide-derived antigens used in the invention and oligonucleotide primers used in amplifying the coding sequence for the gp46-K55 peptide antigen K55-1 (SEQ ID NO: 16) and K55-2 (SEQ ID NO: 17);

FIG. 10 shows, in the upper line, a portion of the HTLV-I genome containing the gp46 envelop protein coding sequence;

FIG. 11 shows a portion of the gp46 coding region containing the sequences which encodes overlapping HTLV-I peptide antigens designated MTA-4, MTA-1, and MTA-5;

FIG. 12 shows amino acid sequences of homologous regions of HTLV-I gp46 (SEQ ID NO: 7) and HTLV-II gp46 (SEQ ID NO: 8) and derived peptides gp46-MTA-1 (SEQ ID NO: 4), GH2-K15 (SEQ ID NO: 6) and gp46-K55 (SEQ ID NO: 5);

FIGS. 15A, 15B, and 15C illustrate a solid-phase assay format for screening for positively identifying HTLV-I or HTLV-II infection, in accordance with another embodiment of the invention, and FIG. 16 shows a solid phase format in an assay test for positively identifying HTLV-I and HTLV-II infection.

DETAILED DESCRIPTION OF THE INVENTION

I. Definitions

Figure 1A:
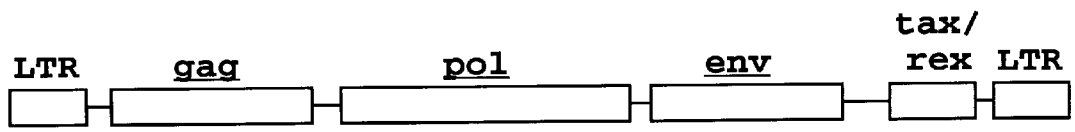
FIGS. 1A–1C show the arrangement of genes in the genomes of HTLV-I and HTLV-II (1A), and the corresponding gene products of HTLV-I (1B) and HTLV-II (1C)

The term "antibody" as used herein, and particularly as used in the context of a therapeutic, describes a protein molecule derived from any of the major vertebrate immunoglobulin classes, such as IgA, IgD, IgE, IgG, or IgM. The term "antibody" is understood to encompass fragments of native antibodies, such as $FAB_2$ fragments and $F_C$ fragments. Antibodies of the invention may be isolated from the serum of a vertebrate, a hybridoma cell, a recombinant eukaryotic, prokaryotic cell, including a plant cell, ascites fluid, bovine milk, or the like. The term "monoclonal antibody" refers to antibodies isolated from a single hybridoma cell or clonal cell line. Such antibodies share a common immunogenic recognition specificity.

The term "antigen" refers to a molecule which is specifically recognized and bound by an antibody. An antigen which elicits an immune response in an organism, as evidenced by production of specific antibodies within the organism is termed an "immunogen." The terms "immunogenic region" or "epitope" are used interchangeably herein to indicate that region of an antigen which is specifically recognized by an antibody.

The "epitope formed by" a given amino acid sequence is the epitope produced by the secondary/tertiary structure of that sequence in aqueous solution.

The "antigen binding site" is that region of the antibody molecule contained within in the variable regions of the antibody which directly participates in binding the antigen.

A specified "peptide antigen containing the epitope formed by" a specified amino acid sequence includes the specified sequence itself or a portion thereof which is sufficient to define the epitope present in the specified sequence, as evidenced by immunoreactivity to a given antibody. The specified peptide antigen may include amino acid substitutions which preserve the epitope.

II. Preparing Human Monoclonal Antibodies

This section describes the preparation of various human monoclonal antibodies used in the invention. The antibodies are obtained from hybridomas are formed by fusion of an anti-HTLV-antibody producing activated human lymphocyte, such as an Epstein-Barr virus transformed lymphocyte, with a stable fusion partner, such as a mouse-human heteromyeloma cell, described below.

A. Isolating Antibody-producing cells from HTLV-positive individuals

HTLV-I infected individuals may be identified by standard procedures, including reactivity of their sera with HTLV antigen p24 and envelope proteins gp46 or gp68, according to standard protocols known in the art. Confirmation of infection is made by polymerase chain reaction (PCR) analysis using HTLV-I specific primers and probes, according to methods known in the art. Likewise, HTLV-II infected individuals are identified by PCR using HTLV-II specific primers and probes (Lipka 1990). In addition, HTLV-II infected individuals can be identified by immunoreactivity of their sera with the recombinant HTLV-II-specific epitope contained within the antigen gp46-K55 (Lipka, 1992).

Although any primate, or particularly, human cells expressing or producing a specific anti-HTLV antibody may be used in producing a hybridoma cell line useful in the invention, B-lymphocytes, such as may be isolated from the spleen or from the peripheral circulation, are preferred sources of antibody-producing cells for hybridoma production. A peripheral blood lymphocyte (PBL) B cell fraction may be isolated from whole blood samples from HTLV-positive individuals, as detailed in Example 1. Anti-HTLV antibody producing cells are then selected and immortalized, as described below, to form a hybridoma cell line for production of monoclonal antibodies which specifically bind unique epitopes of HTLV-I or HTLV-II antigens.

B. Producing Hybridomas from Peripheral Lymphocytes

1. Activation of Lymphocytes

Prior to selection, antibody-secreting B-lymphocytes isolated as described above are activated. Activation is carried out using a transforming virus, such as Epstein-Barr virus, as described in Example 1, or can alternatively be achieved by exposure of the cells to other B-cell activators known in the art, such as pokeweed mitogen, or to the specific antigen recognized by the cells.

Following activation, cells are grown in culture, then examined for production of specific anti-HTLV activity, using an appropriate anti-HTLV antibody detection assay, such as the HTLV-I and HTLV-II viral lysate-based enzyme immunoassays, described in Example 2. Cells showing activity in such an assay are selected for immortalization, by fusion with a heteromyeloma fusion partner, as described below.

2. Fusion with Heteromyeloma Fusion Partner

Formation of a stable hybridoma that secretes a human anti-HTLV antibody is achieved by fusing an activated B-lymphocyte with a hetermyeloma cell such as the K6H6-B5 cell line (Carroll) or the H73C11 cell line (Perkins, 1991), originally produced by fusing activated human lymphocytes with a mouse myeloma fusion partner, as described in Example 3. Such fusion can be achieved by a number of methods known in the art (Harlow) including exposure of mixed cells to polyethylene glycol and exposure of cells to strong electric field (electrofusion), detailed in Example 3. Hybridomas are selected by growth in selective medium, then are tested for HTLV strain and antigen specificity in one or more assays, as described below and in Example 2.

III. Identifying Antigen Specificity of Monoclonal Antibodies

A. Determination of HTLV Strain and Antigen Specificity

Figure 1B:
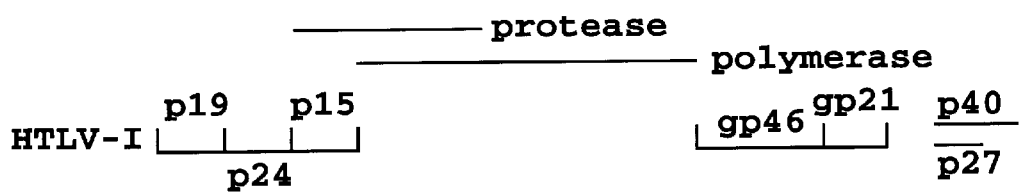
Figure 1C:
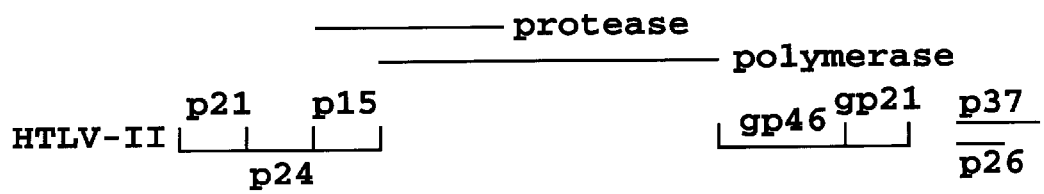

HTLV-I and HTLV-II genomes have been sequenced and gene products identified. The strains share at least 65% nucleic acid homology and 70% amino acid homology (Cann). FIG. 1 shows a diagram of the genomes and known protein gene products of HTLV-I and HTLV-II. In particular, the gag gene products include core proteins of 19 and 24 kilodaltons (p19 and p24) in HTLV-I and 21 and 24 kilodaltons in HTLV-II (p21 and p24). Similarly, the env gene products are 46 kilodalton and 21 kilodalton proteins (gp46 and gp21). The gp46 protein is a cell surface protein that is shed from cells, while gp21 is a transmembrane protein. Human sera reacting with these and other HTLV antigens have been observed.

HTLV strain and antigen specificity of a particular monoclonal antibody may be determined using one or more of a variety of antibody binding assays known in the art (Harlow). Such assays include ELISA assays, such as the viral lysate immunoassay detailed in Example 2A, in which reactivity of an antibody can be determined based on its ability to bind to an antigen or mixture of antigens immobilized on a solid phase. In such assays, the immobilized antigens are chosen to distinguish antibody reactivity to different strains of virus, or, at a more specific level, to different viral antigens.

Figure 5:
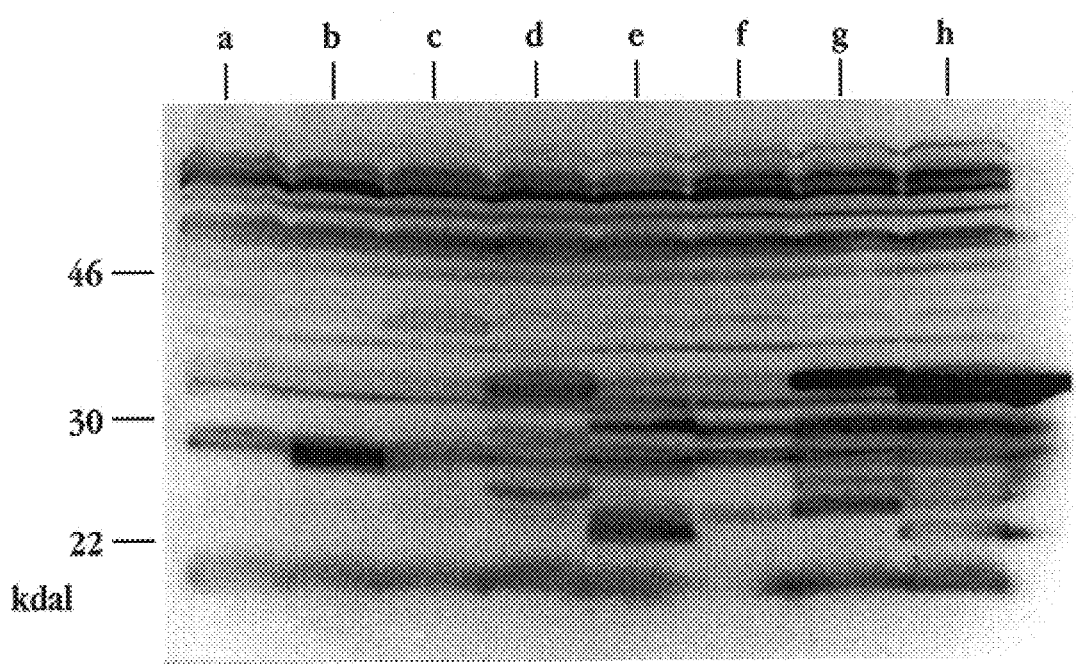
FIG. 5 shows Western blot analyses of incubations of 1/1000 diluted anti glutathione S-transferase sera raised in rabbit on nitrocellulose blots of whole cell lysates of E. coli strain JM101 alone (lane a), E.coli expressing non-recombinant glutathione S-transferase (26.5 kdal; lane b), and (lanes e–h) whole cell lysates of recombinant bacteria expressing fusion proteins p19-FL130 (42.2 kdal; lane c), p19-F86 (36.9 kdal;lane d), p19-F44 (31.8 kdal; lane e), p19-M44 (31.8 kdal; lane f), p19-R45 including the p19-C45 sequence (32 kdal;lane g), and p19-LB27 including the p19-C27 sequence (29.8 kdal; lane h)

Western blots of antigens from a common source separated by SDS polyacrylamide gel electrophoresis (SDS PAGE), such as the Western blot assay described in Example 2B, are particularly useful in distinguishing antigen binding specificity. FIG. 5 shows a Western blot in which human antisera and human monoclonal antibody IH-9 was tested for reactivity with HTLV-I and HTLV-II antigens present in a viral lysate. HTLV-I specificity of the IH-9 antibody is apparent from this blot. The antibody binds to p19 in the HTLV-I lysate, as well as to several of the larger gag precursors, including p55 and p28, but does not bind detectably to proteins in the HTLV-II lysate. For comparison, HTLV-I infected human serum tested against the same antigen profiles reveals the presence of significant amounts of the viral gene products p24 and gp46.

Table 1 summarizes the results of reactivities of a number of human hybridoma supernatants with HTLV-I and HTLV-II infected cells and antigens. Positive reactivity in the immunofluourescence assays of binding to HTLV-I-infected MT-2 cells and to HTLV-II-infected MO-T cells was assessed by binding of a fluorescent-tagged goat anti-human IgG antibody to cells that were preincubated with hybridoma supernatant, as detailed in Example 2C.

In this assay, although many of the monoclonal antibodies exhibited cross-reactivity with HTLV-I and HTLV-II cells, several of the hybridomas, namely WA04/2B10, WA11/2E2, WA07/2D3, WA07/2B10, WA11/1F5, WA11/2C2, WA08/2E9, and IH-9, produced antibodies that were selective for HTLV-I. When binding was assessed in a live cell assay, in which whole, unfixed cells were exposed to antibody (Example 2D), a slightly different pattern was apparent (Table 1). A high level of fluorescence (greater than about 50%), indicating a high level of antibody binding, was observed for WA08/2E9, WA04/2B10, WA07/2F7, WA07/2G3, WA11/2E2, WA07/1G7, WA07/2D3, WA07/2F9, WA11/1F5, and WA11/2F3.

Antigen specificity was assessed by Western blot assay for each of the hybridoma supernatants, as indicated in Table 1. A negative result in this assay may indicate specificity of the antibody for a non-denatured protein; that is, it may indicate that a 3 dimensional protein conformation is required for recognition by the antibody.

TABLE 1

| Antibody | Immuno-fluorescence | | Live Cell[1] | Western[2] | IgG |
|---|---|---|---|---|---|
| | MT-2 | MO-T | Assay (%) | Blot | µg/ml |
| WAIO/3E4 | + | + | 6 | p24 | 0.2 |
| WAO7/2F7 | + | + | 97 | 0 | 52 |

TABLE 1-continued

| Antibody | Immuno-fluorescence | | Live Cell[1] | Western[2] | IgG |
|---|---|---|---|---|---|
| | MT-2 | MO-T | Assay (%) | Blot | µg/ml |
| WAO7/1E4 | + | + | 5 | gp21 | 79 |
| WAO8/2E9 | + | − | 94 | gp21 | 3 |
| WAO7/2B10 | + | − | 51 | gp46 | 3 |
| WAO7/2G3 | + | + | 87 | p24 | 0.6 |
| WA11/2E2 | + | − | 85 | 0 | 9.4 |
| WAO4/2B10 | + | − | 99 | 0 | 35 |
| WAO7/1G7 | + | + | 99 | 0 | 18 |
| WAO7/2D3 | + | − | 98 | 0 | 63 |
| WAO7/2F9 | + | + | 90 | 0 | 16 |
| WA11/1F5 | + | − | 88 | 0 | 6 |
| WA11/2C2 | + | − | 14 | 0 | 66 |
| WA11/2F3 | + | + | 95 | 0 | 30 |
| IH9 | + | − | | p19 | |

Footnotes:
[1]% maximum fluorescence. Values are means of determinations using supernatants from parent cells in culture and spent supernatants from parent cells in culture.
[2]Positive reactivity with protein indicated; 0 = no binding to HTLV proteins; n.d. = not determined.

The hybridoma cell lines which produce these antibodies have been deposited in the Stanford University Blood Bank Viral Immunology Repository, 800 Welch Road, Palo Alto, Calif. 94304. The cell lines are assigned the same repository numbers as have been assigned to the monoclonal antibodies produced. Thus, for example, the deposited cell line which produces the WA08/2E9 antibody is designated WA08/2E9 cell line.

B. Fine-mapping of Antigen Specificity of Monoclonal Antibodies

This section describes experiments carried out to identify the protein or peptide regions which are immunoreactive with the human anti-HTLV monoclonal antibodies of the invention. In general, in order to determine the epitopic specificity, or "fine-map" the antigen specificity, of an antibody, it is necessary to synthesize or recombinantly express specific peptide portions of the antigen. Such peptides can then be employed in solid phase or liquid competition assays, such as ELISA or RIA, to determine specificity of binding.

1. Production of Peptide Antigens

Peptide antigens which are useful in determining epitopic specificity of a monoclonal antibody are formed by any of several methods which are effective to produce small, defined portions of the parent antigenic protein. Thus, limited proteolysis of a viral protein, followed by separation and purification of fragments, or chemical or recombinant synthesis of such defined fragments, for use as components of a fusion protein or alone, are all means of producing peptide antigens useful in fine-mapping epitopic specificity of an antibody.

1a. Recombinant production of peptide antigens

Figure 6:
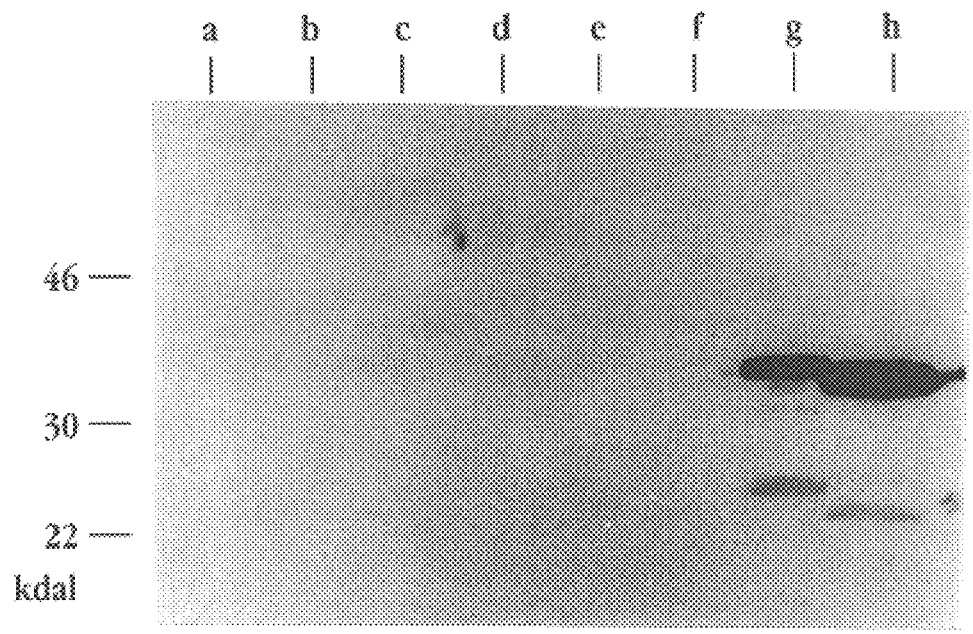
FIG. 6 shows Western blot analyses of incubations of ½ diluted tissue culture supernatant derived from IH-9 HMAb cell line, where lanes (a)–(h) are as in FIG. 5.
Figure 7:
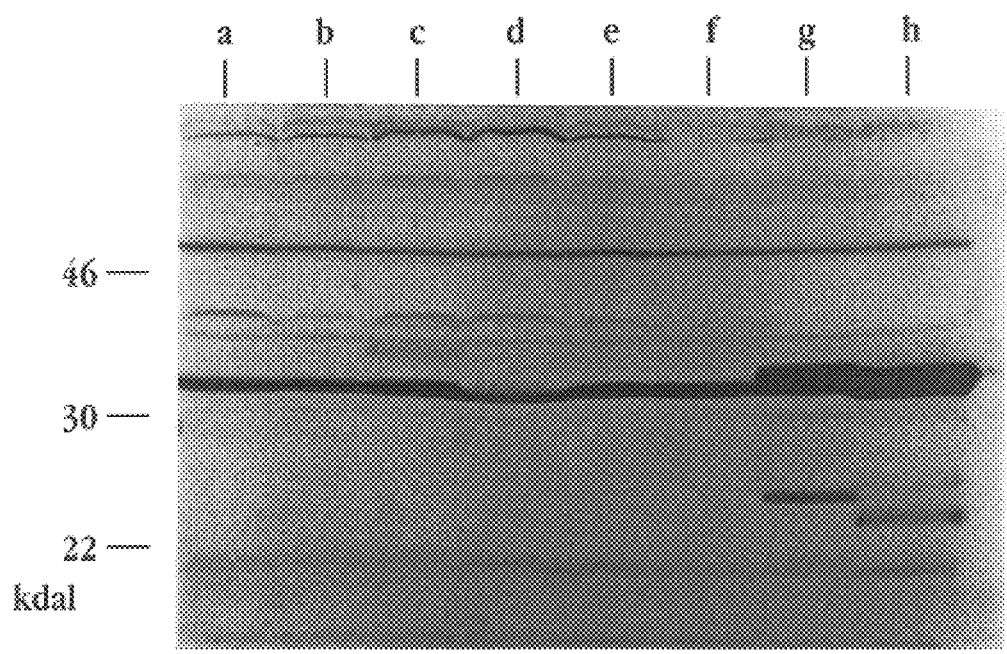
FIG. 7 shows Western blot analyses of incubations of 1/100 diluted antiserum J254, derived from an HTLV-I infected individual, where lanes (a)–(h) as are in FIG. 5 above.
Figure 8:
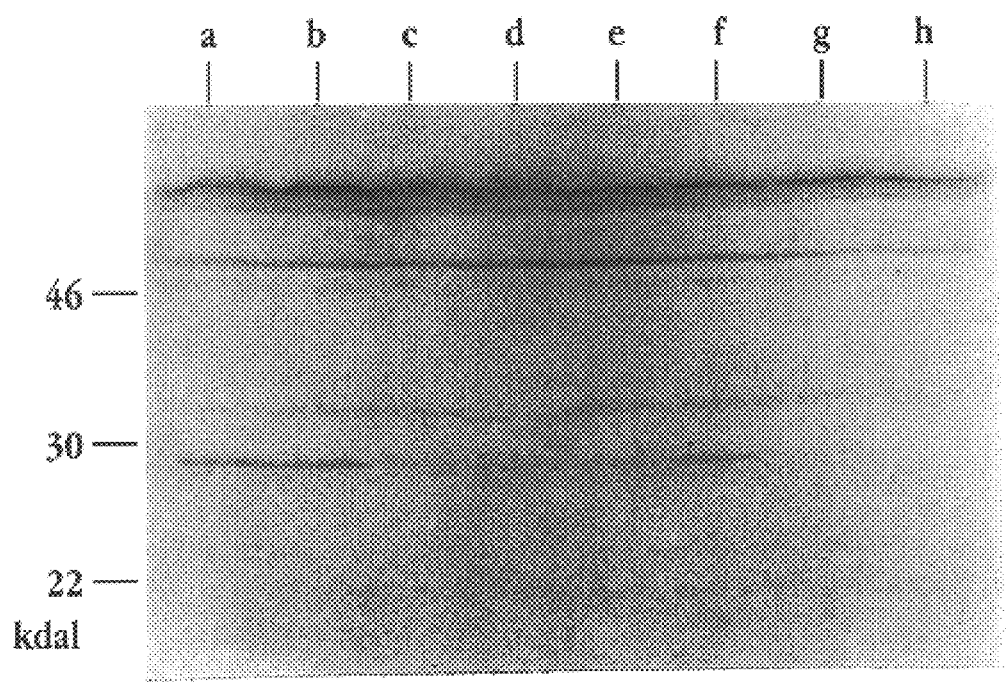
FIG. 8 shows Western blot analyses of incubations of 1/100 diluted antiserum J376, derived from an HTLV negative individual, where lanes (a)–(h) as are in FIG. 5 above.
Figure 9:
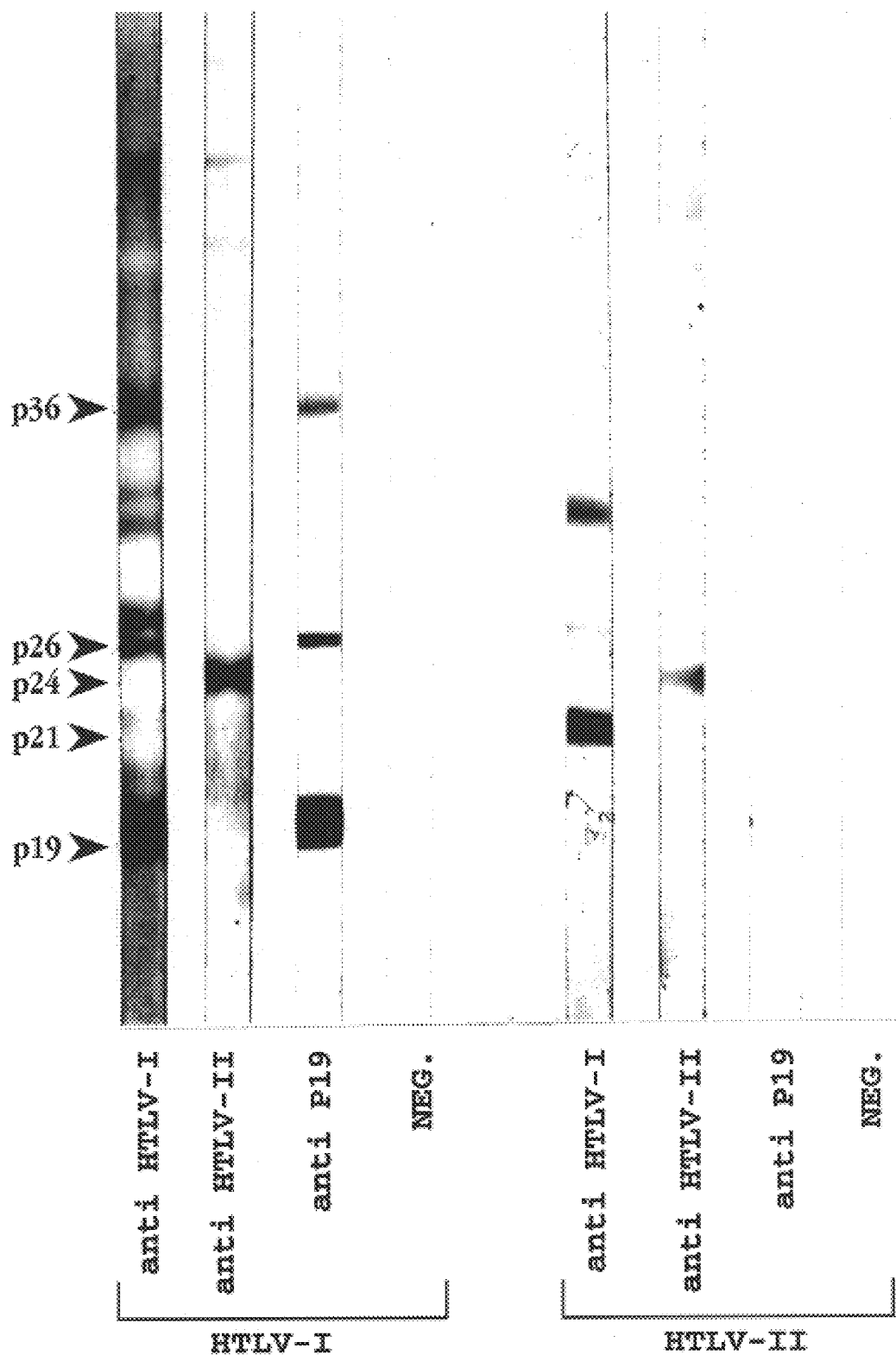
FIG. 9 shows Western blots in which human antisera to HTLV-I and HTLV-II, monoclonal antibody IH-9, and control antisera were tested for reactivity with viral lysates from HTLV-I and HTLV-II-infected cells.

Peptide antigens to be used in the determination of monoclonal antibody specificity may be produced by a variety of recombinant techniques known in the art. Preferred methods of production of recombinant peptides include those in which the resulting peptide product is expressed in a form and location which can be recognized and reached by the antibody molecule. Thus, peptide antigens can be expressed as viral fusion proteins, such as is produced by the filamentous phage fUSE5 expression system, or as bacterial fusion epitope proteins, as described in Example 4 for expression of selected portions of HTLV-I gag protein p19. A similar method has been used in identifying HTLV-II peptide antigens from the HTLV-II gp46 envelope protein. This method is described in co-owned, co-pending U.S. patent application Ser. No. 07/653,091, which is incorporated herein by reference.

In the recombinant method detailed in Example 4, selected portions of HTLV-I p19 were constructed for antigenic screening using the IH-9 antibody. FIG. 3A shows a hydrophilicity plot of the HTLV-I p19 amino acid sequence. Information from such a plot can be used to determine candidate sequences for first round antigenic screening. FIG. 3B shows the relative locations of the peptide fragments constructed. FIG. 3C shows amino acid sequences of two of the immunoreactive peptides expressed in the bacterial fusion protein expression system.

The sequences of the forward and reverse primers used in constructing the p19 coding regions are shown in FIG. 4. Incorporated into each of the primers at the 5' end is endonuclease-specific ligation site, and in this case, an EcoR I ligation site, to facilitate cloning of the amplified DNA molecules. The primers are additionally designed and constructed to facilitate recovery of the open reading frame of the HTLV-I p19 as an in-frame insertion into the vector epression system. The primers shown in FIG. 4 were designed for use with the pGEX (Pharmacia) expression system.

In forming such vectors, polymerase chain reaction (PCR) is performed using an appropriate DNA template. In the case of p19, HTLV-I clone sp65 MT-2 can be used as template. Amplified DNAs are then purified and digested overnight with an appropriate restriction enzyme. Digested DNAs are then ligated into the restriction site of the selected expression vector. In the case of p19, the expression vector is pGEX-2.

Resulting ligated DNA molecules are used to transform competent bacteria, according to standard techniques (Sambrook). Plasmid DNAs from transformed colonies can then be analyzed for the presence of the DNA insert by restriction endonuclease digestion with an appropriate restriction enzyme.

Bacteria transformed with an insert-containing plasmid are screened for correct orientation and protein production by Western blot analysis of crude lysates prepared from cultures of the transformed bacteria, as detailed in Example 4 for transformed *E.coli* containing p19 peptide inserts. Lysate samples are fractionated, in this case by SDS-PAGE, and the fractionated proteins are then blotted onto nitrocellulose filter paper for Western blot analysis. Western blots are screened with the test antibody(ies), in this case the IH-9 HMAb, as well as several antisera from HTLV-I infected and uninfected individuals. Production of recombinant proteins containing non-immunogenic regions of HTLV-I p19 is confirmed through the use of a rabbit antisera containing antibodies directed against non-recombinant glutathione S-transferase, a marker protein which is part of the pGEX vector.

Production of fusion protein by the transformed bacteria may be induced by selective growth conditions, such as by exposure to isopropyl thiogalactoside (IPTG). Following an appropriate growth period, bacteria are lysed and solubilized, if required, by addition of surfactant agents, as well as DNAse I and protease inhibitors. The fusion protein present in the solubilized fraction is then passed through a column containing an appropriate affinity ligand for the constant portion of the fusion protein. In the case of the p19 peptide fusion proteins produced as described in Example 4, the constant portion of the fusion protein, contributed by the vector pGEX, is glutathione transferase. An appropriate affinity matrix for capturing the fusion protein is therefore a glutathione agarose.

Another appropriate fusion protein expression system is the fUSE5 filamentous phage expression system, as described by Cwirla. In this system, an inserted foreign peptide is expressed as a fusion protein in the phage protein coat. In addition this system can be used to produce a random or directed random library of peptides for large-scale screening of short (5–10 amino acid) peptide epitopes (Cwirla, Scott).

The HTLV-II gp46-K55 peptide antigen used in the invention is prepared as follows. A pMO4 plasmid (U.S. patent application for "HTLV-I and HTLV-II Peptide Antigens and Methods", Ser. No. 07/653,091, filed Feb. 8, 1991) was used a source of the gp46 coding sequence. This plasmid contains about 95% of the entire HTLV-II genome. The desired K55 coding region is amplified by plasmid DNA amplification by polymerase chain reaction (PCR), using as PCR primers, the K55-1 and K55-2 primers shown at the bottom in FIG. 4. The two K55 primers are designed to produce amplified K55 coding region with opposite end NcoI/BamHI restriction sites.

The amplified fragments are treated with NcoI and BamHI, and inserted into the NcoI/BamHI sites of a pGEX-GLI plasmid. This plasmid is a modified pGEX-1 plasmid in which the normal EcoRI site has been replaced by closely spaced NcoI and BamHI sites, After fragment insertion, the pGEX-GLI plasmid with K55 coding insert is introduced into a suitable bacterial host for expression of the desired K55 fusion protein.

1b. Synthetic Production of Peptides

Peptides of less than about 50 amino acid residues can also be synthesized using chemical solid-phase synthetic methods, such as are used in commercially available peptide synthesizers. These methods are particularly applicable when the entire amino acid sequence is known, either directly, through amino acid sequencing, or through deduction based on nucleic acid sequence.

Following bulk production, by chemical synthetic methods, purified peptide can be obtained by conventional purification techniques, such as high performance liquid chromatography (HPLC).

2. Binding of Monoclonal Antibodies to Peptide Antigens

Following production of peptide antigens, in accordance with the invention, antibodies are tested for their ability to bind to such antigens. Assays for antibody-antigen binding are well known in the art (Harlow). Solid-phase assays, such as ELISA binding assays are particularly suitable for measuring antibody-peptide binding. Such assays may be carried out in a direct or in a competitive binding assay format. In the direct method, the test peptide is adsorbed to a solid phase. Test anti-HTLV human antibody is added to the peptide, and binding of human antibody to the peptide is measured, for example, in the solid phase HTLV-I lysate enzyme-based immunoassay described in Example 2A.

Alternatively, when peptides are expressed as fusion proteins of sufficient size to be retained by an SDS-PAGE, Western blots may be used to determine binding of the peptide portion of the fusion protein to a specific antibody preparation.

3. Testing expressed fusion epitope proteins for immunoreactivity with IH-9 HMAb The location of the epitope recognized by the IH-9 HMAb was determined by expressing various segments of HTLV-I p19 in a bacterial fusion protein expression system and testing expressed proteins for immunoreactivity with the IH-9 human monoclonal antibody (HMAb) in a Western blot assay. Bacterial whole cell lysates derived from bacteria expressing the HTLV-I p19 antigens presented in FIGS. 5–8 were prepared as described in Example 4. Proteins were fractionated by SDS-PAGE and blotted onto nitrocellulose. As shown in FIG. 6, the blots were incubated with tissue culture supernatant derived from hybridoma culture actively producing IH-9 HMAb, and bound antibody was detected as described in Example 5. As control, FIG. 5 shows the same blots reacted with rabbit polyclonal antisera directed against glutathione S transferase. The presence of strong bands at about 26.5 kilodaltons in all but lane a indicates the presence of glutathione S transferase in these lanes, and hence, confirms expression of a fusion protein. FIGS. 7 and 8 show the reactivities of human polyclonal HTLV-I infected serum and human uninfected serum, respectively.

It is apparent from these results that IH-9 and anti-HTLV-I serum each contain antibodies which react with fusion proteins p19-R45 (32 kdal;lane g) and p19-LB27 (29.8 kdal; lane h). Fusion protein p19-LB27 contains HTLV-I p19-derived peptide p19-C27, identified herein by SEQ ID NO: 1. Fusion protein p19-R45 contains p19-C45, identified herein as SEQ ID NO: 2. Faint immunoreactivity of the IH-9 HMAb toward the full length HTLV-I p19 recombinant p19-FL130 was also observed (lane c). No immunoreactivity toward any of the other HTLV-I p19 recombinant proteins was observed (FIG. 6).

Table 2 summarizes results from similar experiments in which fusion protein p19-R45 was tested for reactivity with HTLV-infected, -indeterminate and uninfected sera.

TABLE 2

Immunoreactivity of fusion protein p19-R45

| Antisera | N | R45 Reactive | % |
| --- | --- | --- | --- |
| HTLV-I infected | 32 | 32 | 100 |
| HTLV-II infected | 32 | 1 | 3.1 |
| HTLV indeterminate, p19 Reactive | 18 | 12 | 66.7 |
| HTLV[b] indeterminate, other | 14 | 0 | 0 |
| HTLV-I negative | 32 | 0 | 0 |

IV. Peptide Antigens for HTLV-I/HTLV-II Assays

This section describes the peptide antigens which are employed in the assay kit and method described in Section IV below. In general the peptides include three pairs of antigens, as described below.

A. HTLV-I and HTLV-II Specific Peptide Antigens

Figure 2A:
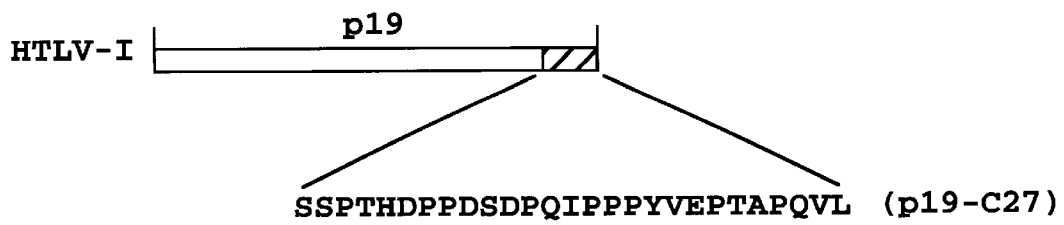
FIGS. 2A–2C show the relative locations and sequences of peptide antigens in p19-C27 (SEQ ID NO: 1) (2A), p21-C27 (SEQ ID NO: 3) (2B), and gp46-MTA-1 (SEQ ID NO: 4) and gp46-K55 (SEQ ID NO: 5) (2C)
Figure 2B:
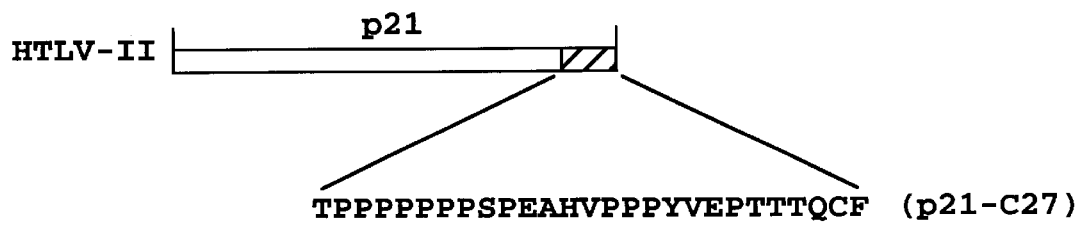

The first pair of antigens includes the HTLV-I specific p19 C-terminal peptide discussed above termed p19-C27 (SEQ ID NO: 1), and the corresponding HTLV-II specific peptide from the HTLV-II core protein p21 termed p21-C-27 (SEQ ID NO: 3). The sequences of these peptides are shown in FIGS. 2A and 2B respectively.

These peptide antigens can be prepared recombinantly, either as fused proteins or as small recombinant peptides, according to methods described above, and in Example 4. Alternatively, the peptide antigens can be prepared by conventional solid-phase synthetic methods.

Studies conducted in support of the present invention, discussed above, demonstrate that the p19-C27 and the p19-C45 peptide antigens are specific for HTLV-I, i.e., the antigens immunoreact with antibodies present in HTLV-I infected individuals, although the two antigens may not detect all HTLV-I positives, and may pick up some false positives, i.e., non-infected individuals. As described above, the p19-C27 and p19-C45 peptide antigens are derived from the C-terminal portion of HTLV-I p19 protein and react with human monoclonal antibody IH-9, characterized above. Similarly, the HTLV-II p21-derived peptide antigen p21-C27 can be expected to detect HTLV-II infection specifically, but may miss some true HTLV-II positives and may select some false positives.

B. HTLV-I and HTLV-II Confirmatory Peptides

The second pair of peptide antigens are derived from internal region of HTLV-I and HTLV-II gp46 env proteins, and have been characterized in co-owned U.S. Pat. No. 5,066,579, and co-owned U.S. patent application for "HTLV-I and HTLV-II Peptide Antigens and Methods", Ser. No. 07/653,091, filed Feb. 8, 1991, both of which are incorporated herein by reference.

Figure 2C:
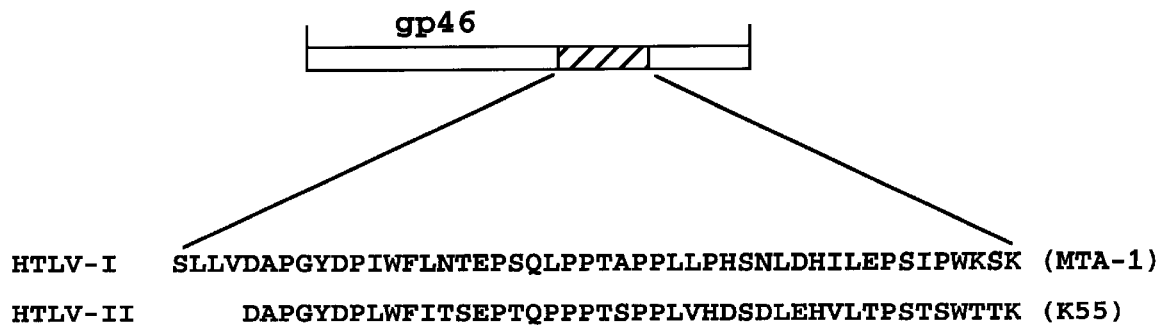

FIG. 10 shows, in the upper line, a portion of the HTLV-I genome containing the gp46 envelope protein coding sequence, and in the lower line, a portion of the gp46 coding region containing the sequences which encode overlapping HTLV-I peptide antigens formed in accordance with the invention. These peptides are designated MTA-4, MTA-1, and MTA-5 in FIG. 11. All of the sequences fall within base pairs 5565 and 5895 of the HTLV-I genome, within the gene coding for the HTLV-I envelope protein gp46, and have an overlapping coding sequence between base pairs 5664 and 5709. The overlapping sequence codes for a 42-amino acid peptide antigen having the following sequence: which are the first 42 amino acids of the MTA-1 peptide (SEQ ID NO:4). Screening studies conducted in support of the invention indicate that the MTA-1 peptide picks up the highest percentage of HTLV-I positive sera, particularly among subjects of Japanese ancestry. As seen in FIG. 2C, the MTA-1 peptide includes the additional Ile-Pro-Trp-Lys-Ser-Lys residues at the Ser C-terminus of the above sequence. In a preferred embodiment of the invention, the HTLV-I gp46 confirmatory peptide antigen contains the immunogenic region of the C-terminal 48 amino acid MTA-1 sequence which is immunoreactive with the 0.5α Mab.

More generally, the HTLV-I gp46 confirmatory peptide antigens of the invention include the immunogenic region of the above amino acid sequence which is immunoreactive with the .5α Mab. As defined herein, the specified sequence includes minor, neutral amino acid substitutions which do not appreciably decrease the immunoreactivity of the peptide antigen for the .5α Mab. Such amino acid substitutions may be selected on the basis of similarities in hydrophobicity, size, charge, hydrogen bonding ability, and effect on secondary structure according to known amino acid substitution principles. FIG. 2C shows the amino acid sequence of the MTA-1 peptide, which has been designated gp46-MTA-1 peptide (SEQ ID NO: 4) derived from HTLV-I p46 protein. An HTLV-II peptide designated GH2-K15 (FIG. 12) corresponding to the HTLV-I peptide MTA-1 was prepared by cloning of an HLTV-II coding sequence corresponding to the desired peptide sequence. A 147 base pair (bp) HLTV-II DNA fragment corresponding to nucleotides 5648 to 5794 of the HTLV-II genome was originally amplified from the HTLV-II clone pM04 (which contains the majority of the HLTV-II genome cloned into the BamH I site of the plasmid pBR322) by use of the polymerase chain reaction (PCR) procedure (Perkin Elmer/Cetus GeneAmp kit).

In a preliminary experiment, sera from approximately 200 individuals with PCR-confirmed HTLV-I or HTLV-II infection, as well as sera from approximately 150 uninfected individuals were paneled against the GH2-K15 antigen. 98% of the sera from HTLV-II infected individuals reacted with GH2-K15. None of either the HLTV-I infected sera or the uninfected sera reacted with GH2-K15. The screening results demonstrate that the GH2-K15 peptide is specifically immunoreactive with HTLV-II positive sera. Sequences corresponding to similar regions of HTLV-II p46 protein, designated GH2-K15 (SEQ ID NO: 6) and gp46-K55 (SEQ ID NO: 5) are also shown in the figure.

HTLV-I and HTLV-II gp46 peptide antigens are produced recombinantly as β-galactosidase fusion proteins from genomic libraries of HTLV-I and HTLV-II, as described in co-owned PCT Publication Number WO 89/06543, published Jul. 27, 1989. Alternatively, the peptides can be produced as fusion peptides using the vectors and methods detailed for production of the p19 peptide antigen in Example 4. Peptides can also be produced by solid phase chemical synthetic methods, as discussed above.

Currently, in the U.S., standard criteria for infection by HTLV include reactivity with HTLV-I envelope protein gp46 or precursor protein gp68 in conjunction with reactivity with p24 antigen. This test does not, however, distinguish between infection by HTLV-I and HTLV-II. Certain peptides derived from the HTLV-I p46 envelope protein of HTLV-I were shown to be useful in confirming infection of a patient by the HTLV-I, in conjunction with p24 reactivity present in the serum, in previously cited co-owned U.S. patent application Ser. No. 07/653,091 for "HTLV-I and HTLV-II Peptide Antigens and Methods" and in U.S. Pat. No. 5,066,579. These peptides are characterized as immunoreactive with monoclonal 0.5α produced by hybridoma cell line ATCC Number HC8755 (Matsushita). Furthermore, it was shown that serum immunoreactivity with these gp46-derived peptides are indicative of HTLV-I infection of the serum.

Similarly, as disclosed in U.S. patent application Ser. No. 07/653,091, a peptide GH-K15 derived from a portion of the HTLV-II gp46 molecule homologous to the HTLV-I gp46-MTA-1 peptide region described above, can be used to confirm HTLV-II infection of human sera. The gp-46-MTA-1 and gp46-K15 peptides have been previously reported in co-owned patent applications, and do not, by themselves, form part of the present invention. However, the gp46-K55 peptide described above, which allows for high levels of expression of recombinant HTLV-II specific portion of the gp46 protein, does form part of the present invention.

In accordance with the present invention, reactivity of antibodies in a test serum with the p19 antigen (e.g., p19-C27 or p19-C45) or with the analogous HTLV-II p21 antigenic region (e.g., p21-C27), in conjunction with reactivity with HTLV-I gp46-derived peptide gp46-MTA-I or to the corresponding HTLV-II-specific gp46 peptides gp46-K55 or GH2-K15, increases significantly the reliability of diagnosis of HTLV-I or HTLV-II infection.

C. Immunodominant HTLV-I/HTLV-II Antigens

Gene products of HTLV-I and HTLV-II virions include gag gene product p24, a core protein, and env gene product gp21, an envelope transmembrane protein which are fairly highly conserved between the two strains.

According to current diagnostic criteria, immunoreactivity with p24 and one of the envelope proteins (usually gp46) is considered diagnostic of HTLV-I or HTLV-II infection; however, this immunoreactivity pattern still results in a significant proportion of false positives, and does not distinguish between the two strains. More recently, recombinant envelope protein p21e derived from HTLV-I gp21 has been included as an envelope diagnostic element in the diagnosis of HTLV infection (Lillehoj). This protein, used alone or in combination with p24, does not distinguish between HTLV-I and HTLV-II.

Monoclonal antibodies developed in support of the present invention recognize specific epitopes of p24, gp21/p21e, as listed in Table 1. These specific epitopes can be identified by methods similar to those described above for identification of the portion of the p19 HTLV-I cap protein which is immunoreactive with the IH-9 antibody.

V. Assay Kits and Methods

This section will describe representative kit formats useful in screening human sera for presence of HTLV-I or HTLV-II infection and in differential diagnosis between HTLV-I and HTLV-II infections, using the peptide antigens described above.

A. Screening Kit and Assay

Figure 13A:
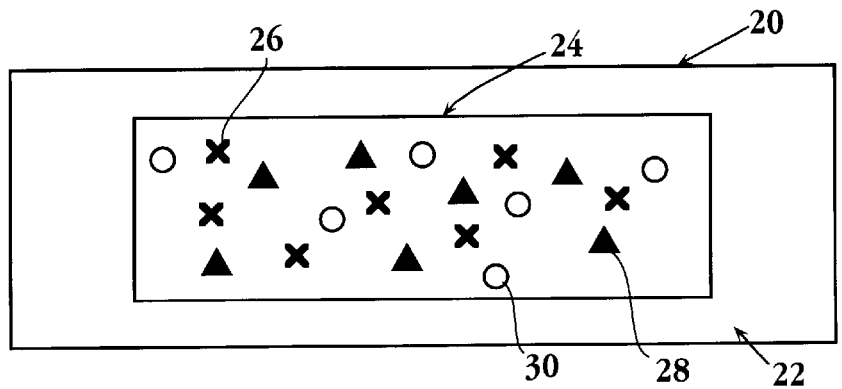
FIGS. 13A–13C illustrate the steps in a method for screening human serum for the presence of HTLV infection, in accordance with one embodiment of the invention.

FIG. 13A shows a representative solid phase test kit useful in screening for the presence of HTLV-I or HTLV-II infection. A solid support strip 20 in the kit includes a backing 22 and a reaction region 24 to which is bound HTLV-I and HTLV-II peptide antigens, as described below. The backing 22 is preferably formed of a nonpermeable optically transparent rigid plastic material. The reaction region 24 is formed of a peptide-adherent material, such as polyethylene or polyvinylchloride, as is commonly used in ELISA plates, to which peptide antigens can be conveniently adsorbed. Alternatively, reaction region 24 may be a membrane, such as a nitrocellulose membrane, an activated nylon membrane or other derivatized membrane suitable for binding proteins or peptides.

After antigen immobilization on the reaction region, such as by antigen absorption, remaining protein/binding sites are blocked by incubation with excess non-reactive peptide or protein reagent, such as BLOTTO reagent or bovine serum albumin, according to methods known in the art.

With further reference to FIG. 13A, the method of detection of the presence of infection by HTLV-I or HTLV-II, as embodied in the illustrated test kit, includes the presence of at least three distinct peptide antigens immobilized on the reaction region, represented in the figure by different symbols, 26, 28, and 30. Either of antigens gag protein p24 or env protein gp21, or their respective specific peptide epitopes defined by immunoreactivity with human monoclonal antibody WA07/2G3 (p24) and human monoclonal antibody WA07/2F7 or WA07/1E4 (gp21) described in Section III above, is present in the reaction region, as indicated at 26 in FIG. 13A. As described above, these antigens are immunodominant HTLV antigens and reactive with sera from persons having HTLV-I or HTLV-II infections, but fail to recognize all seropositive individuals and may also select false positives.

The reaction region additionally includes peptide antigens specific to HTLV-I and HTLV-II virions, which have been shown, in accordance with the invention to detect additional seropositive individuals. As illustrated in FIG. 13A, peptide antigen 28 represents one or both of the HTLV-I-specific peptide antigens p19-C27 and gp46-MTA-1. Peptide antigen 30 represents one or both of the HTLV-II-specific peptide antigens p21-C27 and gp46-K55. That is, the reaction region includes at least one of the peptide antigens p24 or gp21 (or immunoreactive portions thereof) and at least one of the following pairs of antigens : (1) p19-C27 and p21-C27 or (2) gp46-MTA-1 and gp46-K55.

Figure 13B:
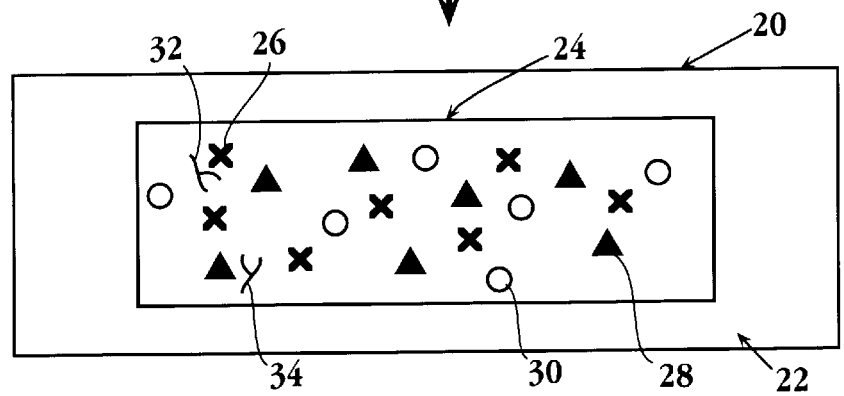
Figure 13C:
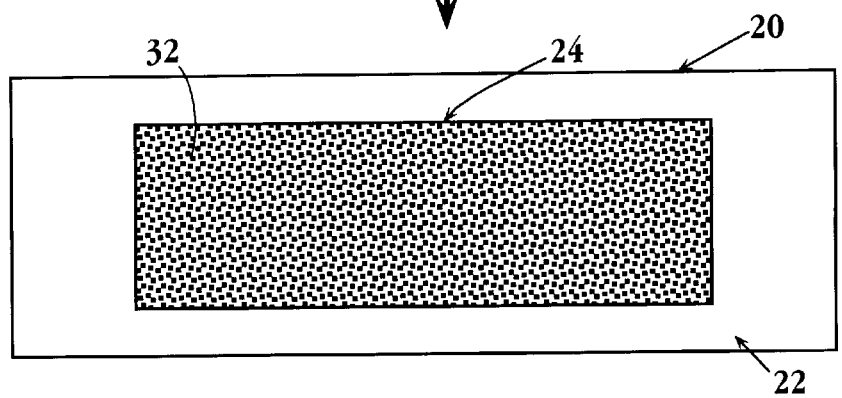

In accordance with the invention, and as illustrated in FIG. 13, test serum is applied to the test kit so that it contacts reaction zone 24. There, test serum antibodies directed to one or more of the antigens 26, 28, 30 present in the reaction zone bind to the antigen. As illustrated in FIG. 13B, antibody 32 present in a test serum from an HTLV-I infected individual binds to one or more of the three different peptides immobilized on the test strip reaction region. Completing the sequence of the use of the test kit as illustrated, the strip is washed to remove antibody bound non-specifically to the reaction zone, and a detection reagent, or means, such as a radiolabeled or fluorescent-labeled goat-antihuman immunoglobulin reagent, in the kit, is added to the zone, to produce a signal 32, as illustrated in FIG. 13C for detection of bound antibody. The detection reagent may alternatively include reporter-labeled antigens which are immunoreactive with the serum antibodies, in a sandwich-assay format of the type described below.

As can be appreciated, the screening kit will detect all sera containing the immunodominant p24 or gp21 antibodies and, in addition, sera which fail to have immunodominant antibody, but which have an HTLV-I-specific antibody (to either p19-C27 or to gp46-MTA-1 peptide antigens) or an HTLV-II specific antibody (to p21-C17 or gp46-K55 peptide antignes).

A positive reaction in the screening test kit described does not distinguish between HTLV-I and HTLV-II infection. A modification of the screening test kit, in which reporter molecules used in the detection step can be distinguished one from another, based on specific immunoreactivity with an HTLV-I or an HTLV-II epitope, can be used to discriminate between the two infections. Such immunospecific reporter molecules are described in conjunction with one of the embodiments of the HTLV confirmatory test kits, below.

B. Confirmatory Kits and Assays

FIGS. 14A–14D illustrate a test kit and assay for positive identification of HTLV-I infection in an HTLV-seropositive human serum. The test kit includes a solid support strip 34 having a backing 36 and reaction zones 38 and 40 in which are immobilized antigens from HTLV-I specific regions of gag protein p19 (indicated at 42 in region 38) and env protein p46 (indicated at 44 in region 40). As illustrated in a preferred embodiment, the p19 antigen 42 contains the epitope formed by the amino acid sequence SEQ ID NO: 1, which is immunoreactive with human monoclonal antibody IH-9, and the p46 antigen contains the epitope formed by the amino acid sequence SEQ ID NO: 4.

Figure 14A:
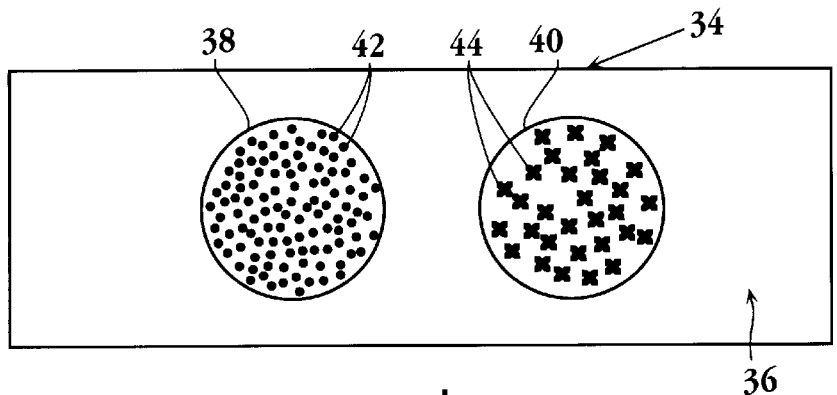
FIGS. 14A–14C illustrate the steps in a method for positively identifying HTLV-I infection from human serum, in accordance with another embodiment of the invention.
Figure 14B:
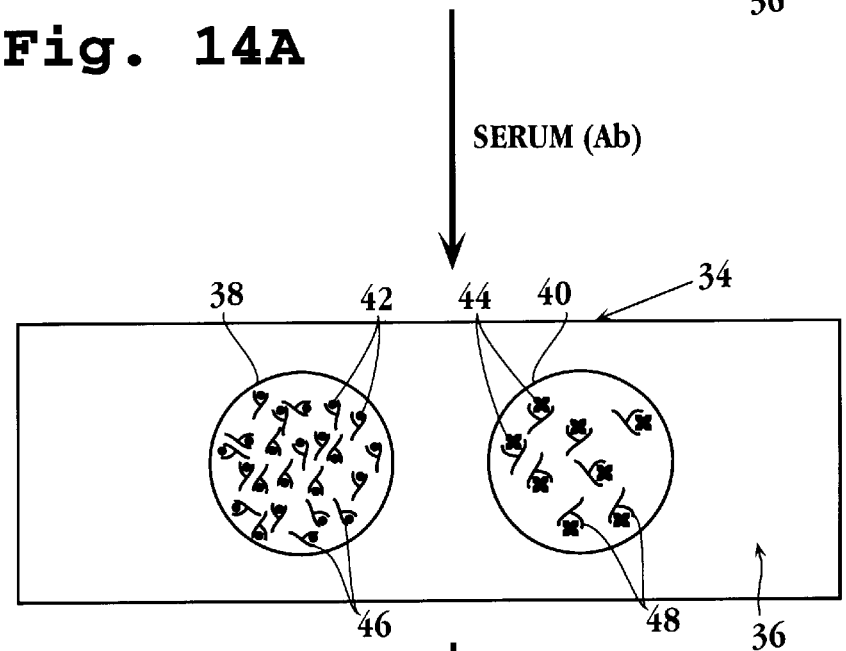
Figure 14C:
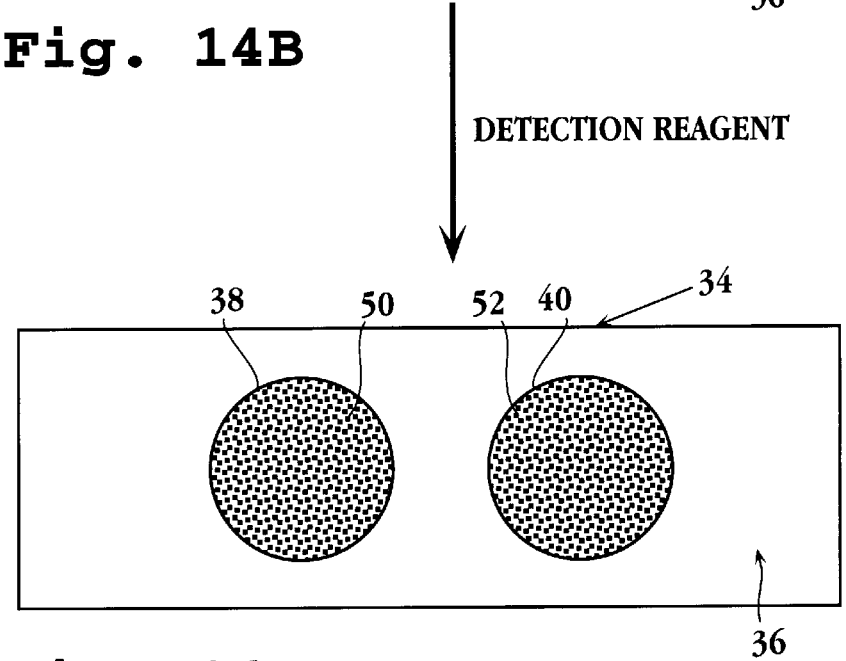

In accordance with the assay method and test kit illustrated in FIGS. 14A–14C, a human test serum is contacted with the reaction zones 38 and 40, and antibodies 46, 48 present in the serum bind to antigens 42 and 44, respectively. Detection of bound human immunoglobulins is made by addition of a detection reagent, or means, such as labeled goat anti-human antibody, to produce detection signals 50, 52 illustrated in FIG. 14C. Confirmation of HTLV-I immunoreactivity with both antigens serves as positive identification of HTLV-I infection of human donor of the test serum.

Alternatively, the detection reagent may include an HTLV-I p19 peptide antigen containing the epitope formed by the amino acid sequence SEQ ID NO: 1, and labeled with a detectable reporter, and (b) an HTLV-I gp46 peptide antigen containing the epitope formed by the amino acid sequence SEQ ID NO: 4 and labeled with a detectable reporter.

A similar kit for positive identification of HTLV-II infection includes, as the antigen identified at 42 in FIGS. 14A–14C, an HTLV-II p21-C27 antigen containing the epitope formed by the amino acid sequence SEQ ID NO: 3; and as the antigen identified at 44 in the figures, an HTLV-II gp46-K55 peptide antigen containing the epitope formed by the amino acid sequence SEQ ID NO:5.

It can be further appreciated that the HTLV-I-specific antigens, described with reference to FIG. 14 above, can both be present in a single reaction zone 58 carried on a backing 56 on a strip 54 as illustrated in FIG. 15A. In this embodiment, antigen 62 represents the HTLV-I specific p19 peptide antigen described above, and antigen 64 represents an HTLV-I specific p46-derived peptide also described above. Alternatively, the test antigens 62, 64 may be the corresponding HTLV-II antigens p21 and pg46, as above.

FIG. 15B shows an enlarged side view of reaction zone 58, with bound p19 and p46 antigens, and bound human serum antibodies 66, 68, after contact of the reaction strip with human HTLV-I positive test serum. After reacting the antibodies with the reaction region on the strip, the test strip is reacted with a detecting reagent, or means in the kit.

The detecting reagent includes an HTLV-I p19 peptide antigen containing the epitope formed by the amino acid sequence SEQ ID NO: 1, and labeled with a detectable reporter, and (b) an HTLV-I gp46 peptide antigen containing the epitope formed by the amino acid sequence SEQ ID NO: 4 and labeled with a detectable reporter. The p19 detection molecule, indicated at 70, includes a reporter (*) indicated at 72, and the MTA-1 detection molecule, indicated at 74, includes a reporter (#) indicated at 76. The two reporters are distinguishable when bound to a common region. Exemplary reporters include two distinguishable fluorescent reporters having different absorption/emission peaks, such as are commonly used in DNA sequencing.

FIG. 16 illustrates a kit 78 for positive identification of HTLV-I and HTLV-II infection in a human serum sample. Here, the solid support 80 includes four reaction zones 82, 84, 86, 88. Each reaction zone contains, immobilized thereon, one of the HTLV-I- or HTLV-II-specific antigens discussed above. As illustrated, reaction zone 82 contains p19 antigen 90, reaction zone 84 contains p21*** peptide antigen 92, reaction zone 86 contains MTA-I peptide antigen 94, and reaction zone 88 contains K55 peptide antigen 96. Methods for contacting human test sera and reporter molecules with the test kit are as described for the test kits illustrated in FIGS. 13–15, above. Positive confirmation of HTLV-I infection is made when a detectable, immunoglobulin-specific signal is detected in regions 90 and 94; positive identification of HTLV-II infection can be made when a positive signal is detected in regions 92 and 96.

V. Vaccine Composition and Method

This section describes the use of the human anti-HTLV-I monoclonal antibodies (Mabs) described in Section II for use in immunoprophylaxis and for identifying peptide antigens which are effective in vaccine compositions for immunizing humans against HTLV-I infection.

A. Immunoprophylaxis

In this embodiment, the invention includes an antibody vaccine composition effective in neutralizing HTLV-I infection, as evidenced by the ability of the composition antibodies to bind to cultured cells infected with HTLV-I. In this approach, human Mabs specific against HTLV-I antigens which are expressed on the surface of HTLV-I-infected are administered into the blood stream of an infected individual. Binding of these antibodies to HTLV-I-infected cells then provokes a humoral immune response in which macrophages destroy B lyphocytes having bound anti-HTLV-I antibodies.

The antibodies in the composition include one or more of those described above which are found to have high levels of binding to HTLV-I infected cells in culture as detailed above (Table I). These include the monoclonal antibodies designated WA07/2F7, WA08/2E9, WA07,2G3, WA11/2E2, WA04/2B10, WA07/1G7, WA07/2D3, WA07/2F9, WA11/1F5, and WA11/2F3. The antibodies are obtained as human monoclonal antibodies, as detailed above.

The anti-HTLV-I antibodies are formulated in a suitable solution for injection, typically by parenteral route, to form the vaccine composition. Vaccination may be prior to an expected infection, or in treating existing HTLV-I infection. In one general application, infants whose mothers are diagnosed as having HTLV-I are injected with the antibody composition, to prevent development of the viral infection, particularly when the infant is breast fed over an extended period. The antibodies may be administered parenterally, e.g., intramuscularly, subcutaneously, or intravenously, or in the case of infants, also by oral administration, in a method for treating or preventing HTLV-I by immune prophylaxis.

B. Peptide Antigen Vaccine Composition

The invention also contemplates a peptide antigen vaccine composition for use in immunizing an individual against HTLV-I infection. The vaccine composition includes peptide antigen(s) which are immunoreactive with one or more of the neutralizing antibodies WA07/2F7, WA08/2E9, WA07, 2G3, WA11/2E2, WA04/2B10, WA07/1G7, WA07/2D3, WA07/2F9, WA11/1F5, and WA11/2F3 described above. One of these immunoreactive peptides is the above p19-C27 or p19-C45 peptide antigens derived from the C-terminal region of the HTLV-I p19 gag protein.

Suitable immunoreactive peptide antigens to the above human monoclonal antibodies can be identified substantially as described for the p19 antigen. Briefly, there is formed an library of HTLV-I genomic fragments capable of expressing in a suitable host system, HTLV-I peptides, preferably in the range of about 30–100 amino acids. One preferred expression system is the above gtll library vector which makes a fusion protein with genomic inserts.

The library is screened with each of the above Mabs to identify expression vectors whose expressed genomic fragments are immuoreactive with the peptides. After subcloning to isolate library clones which synthesize immunoreactive peptides, the cloned genomic fragment may be further fragmented to fine map the peptide antigen which contains the immunoreactive epitope.

The peptide antigens, once identified, may be covalently coupled to a carrier protein, such as keyhole limpet hemocyanin, and injected either in solution form or in combination with an adjuvant. Alternatively, where the HTLV-I antigen is prepared as part of a fusion protein, the non-HTLV moiety of the protein may serve as the carrier protein. The derivatized or fusion protein is carried in a pharmaceutically acceptable carrier, such as in solution or in an adjuvant, such as converted alum.

Alternatively, the free peptide antigen itself may be formulated in alum or used without adjuvant. A suitable adjuvanted vaccine has a preferred antigen concentration of about 1 mg peptide antigen/mg alum, but not to exceed 80$\mu$ of alum per injection.

In a related aspect, the invention is directed to a method of inhibiting infection of an individual by HTLV-I virus, by administering to the subject, by parenteral injection, the peptide antigen vaccine composition described above.

One preferred vaccine compositions, for use in the method are those in which the HTLV-I antigen includes the sequence in the peptides identified by Sequence ID No. 1.

The following examples illustrate, but in no way are intended to limit, the present invention.

Materials and Methods

Materials

Cells and Media: (SOURCES, Growth conditions) Cell culture media (PFHM, RPMI, IMDM) were obtained from Gibco Laboratories (Grand Island, N.Y.). EBV-activated B cells, the mouse-human heteromyeloma H72C11 (kindly provided by J. Larrick, GLI, Redwood City, Calif., USA), and hybridomas were grown in a 37° C. incubator with 6–6½% $CO_2$ in complete Iscove's Modified Dulbecco's Medium (IMDM, Gibco, Grand Island, N.Y., USA). For B cell activation, peripheral blood lymphocytes were isolated by Hypaque-Ficoll gradient centrifugation (Boyum, 1968). B cells were separated from T cells by rosetting with AET-treated sheep red blood cells (Saxon et al., 1976) and activated with EBV from the B95-8 marmoset line, as previously described (Perkins et al., 1989).

Fusion media contained 1 mg/ml pure bovine serum albumin (Serva Biochemicals, Westbury, N.Y., USA), 0.5 mM $Mg^{2+}$ acetate (E.M. Science). Sorbitol (E.M. Science) was used at a range of concentrations to vary the osmolarity. Isoosmolar medium (300 L3) contains 280 mM sorbitol for a final osmolarity of 300 mOsmol. Hypoosmolar medium (75 L3 and 100 L3) contains 70 and 93 mM sorbitol for final osmolarities of 75 and 100 mOsmol, respectively.

MT-2 cells (Miyoshi) are infected with HTLV-I virus. MO-T cells are an HTLV-II-infected cell line described by Chen.

Construction of K6H6-B5 mouse-human heteromyeloma cells is described by Carroll; these cells were obtained from Dr. Ronald Levy, Department of Medicine, Stanford University Medical School, Stanford, Calif. 94305.

Antisera used in experiments supporting the invention included a well characterized panel of sera from 32 HTLV-I, and 32 HTLV-II infected individuals, as described by Lipka. All of the HTLV-I and most of the HTLV-II sera had antibody profiles meeting standard criteria for HTLV infection (antibodies to p24 gag and gp46 and/or gp68 env proteins). In addition, the sera were typed as being HTLV-I infected both by positive reactivity toward the recombinant HTLV-I antigen MTA-1, a recombinant antigen containing amino acids 163-209 of HTLV-I gp46 protein (Lipka) and by PCR analysis using HTLV-I specific oligonucleotide primers and probes.

Similarly, 32 HTLV-II infected individuals were identified by their reactivity towards the recombinant HTLV-II antigen K55 and by PCR using HTLV-II specific primers and probes. Recombinant antigens containing the epitope recognized by the IH-9 HMAb were also tested for their reactivity with HTLV negative sera and HTLV indeterminate serum samples. All of the indeterminate sera were reactive with commercially available HTLV screening tests, but were negative for HTLV DNA when tested by PCR using HTLV-I or HTLV-II specific primers and probes (Kwok, Lipka, 1991). These sera included sera with antibodies directed to HTLV-I p24, recombinant antigen p21E, and 18 sera which reacted with HTLV-I, when tested with p19 antigen (Lipka, 1991). Sera from HTLV-I and HTLV-II infected individuals were obtained from multiple sources, including Stanford University Blood Bank, as well as other U.S. blood banks. All HTLV-I-indeterminate and uninfected sera samples were from the Stanford University Blood Bank.

Rabbit anti-glutathione transferase antiserum was produced in New Zealand white rabbits. This antiserum was custom produced by Joslyn Laboratories, Santa Rosa, Calif., using non-recombinant glutathione transferase (Sigma) as antigen.

EXAMPLE 1

Isolation and Epstein-Barr Activation of Peripheral B Lymphocytes from HTLV-I-infected Individuals Peripheral Blood Lymphocytes (PBL) were isolated from an asymptomatic HTLV-I infected individual and activated with Epstein-Barr virus (EBV) essentially as described by Foung and Perkins and as described below.

A. Isolation of Lymphocytes

Whole blood samples (15 ml) were centrifuged at 2000 rpm for 5 minutes in a clinical centrifuge. Supernatant plasma was removed, and packed cells (5–10 ml packed volume) were suspended in 35 ml RPMI medium. The cell suspension was underlayed with 13 ml Histopaque (Sigma), then centrifuged at 2500 rpm for 25 minutes. Cells present in a turbid interface layer (between Histopaque and buffer) were collected, suspended in RPMI, and centrifuged (1000 rpm, 10 min). Pelleted cells (PBL) were then resuspended in RPMI containing 10% fetal calf serum (FCS) to a final cell concentration of about $3 \times 10^6$ cells/ml.

B. Isolation of monocyte depleted PBLs

Monocytes present in the PBL fraction were depleted from the fraction by incubation of the PBL suspension in several large culture T-flasks at 37° for 60 minutes. Nonadherent cells were collected by aspiration, then centrifuged (1000 rpm, 10 min). Resulting cell pellets were suspended in RPMI +10% FCS at a concentration of approximately $5 \times 10^6$ cells/ml.

C. Depletion of T-lymphocytes from PBLs by rosetting

A sheep red blood cell (SRBC) fraction was purchased from Colorado Serum Company. Five milliliters of AET-treated SRBC were added to PBLs suspended in RPMI +10% FCS, as described above, and the mixture was centrifuged at 200 rpm for 5 minutes in a clinical centrifuge, then placed on ice for 30 minutes. The pellet was gently mixed, with the supernatant, then underlayed with Histopaque, followed by centrifugation at 2500 rpm for 30 minutes. E⁻ lymphocytes (B-lymphocytes) were collected from the interface between the Histopaque and the buffer and were suspended in RPMI. The B-cell suspension was centrifuged (1000 rpm, 10 minutes) and the resulting cell pellet was suspended to a concentration of approximately $5 \times 10^6$ cell/ml in IMDM +30% FCS.

D. Activation of B-Lymphocytes with Epstein-Barr Virus (EBV)

B-lymphocytes were suspended in IMDM +30% FCS, then mixed with 1 ml culture supernatant from an EBV-infected marmoset cell (B958) culture (Perkins 1989).

Activated cells were plated at a density of 10⁴ cells per well in a 96 well cell culture plate (Corning, Corning, N.Y.) in a medium consisting of IMDM, 30% fetal calf serum, and 2%-mercaptoethanol. After 17 days in culture, specific anti-HTLV-I $I_gG$ activity was assessed using an HTLV-I viral lysate-based enzyme immunoassay, described in Example 2.

EXAMPLE 2

Assay of anti-HTLV-I and anti-HTLV-II Immunoglobulins

A. HTLV-I and HTLV-II lysate Enzyme-based Immunoassay

HTLV-I viral lysate Enzyme-based immunoassays were obtained from commercial sources (either Abbott Laboratories, North Chicago, Ill. or DuPont, Wilmington, Del.), and assays were performed following manufacturers' instructions.

B. Western Blot analysis of anti-HTLV-I Antibodies

Antigenic specificity of isolated anti HTLV-I monoclonal antibodies was determined using an HTLV-I viral lysate based Western Blot (WB). HTLV-I viral lysate was derived from HTLV-I infected MT-2 cell line and HTLV-II viral lysate from the MoT cell line were obtained from Hillcrest Biologicals (Cypress, Calif.) Following electrophoresis (SDS-PAGE), the gel-separated proteins were blotted onto nitrocellulose filter paper (Schleicher and Schuell), essentially as described by Lipka. The nitrocellose blot was incubated overnight at room temperature with hybridoma culture supernatant or HTLV-I infected or control antisera diluted in blotto (10 mM TRIS-HCl, pH 7.4, 5% nonfat dry milk, 2.5% normal goat sera, and 0.5% Tween-20). Strips of the nitrocellulose blot were washed 3 times with wash buffer (10 mM TRIS-HCl pH 7.4, 0.05% Tween-20) for 5 minutes each. Bound human immunoglobulin G (IgG) was detected by a 1 hour incubation with goat-anti-human IgG conjugated to alkaline phosphatase (Immun-Blot, Bio-Rad), for 1 hour. This was followed by three more 5 minute rinses. Bound second antibody was detected by incubating the strips in a substrate solution containing 5-bromo-4-chloro 3-indolylphosphate (BCIP) and Nitroblue tetrazolium (NBT) in 100 mM TRIS-HCl, pH 9.5, and 50 mM $MgCl_2$.

C. Detection of antibody binding to HTLV-I and HTLV-II infected cells by immunofluorescence MT-2 cells are an HTLV-I infected cell line described by Miyoshi. MO-T cells are an HTLV-II cell line described by Chen.

MT-2 Immunofluorescence. MT-2 cells were co-cultured with H-9 cells at a ratio of 1:3 (MT-2:H-9) on microscope slides in RPMI medium supplemented with 10% fetal calf serum to confluency, then stored frozen at −72° until use. Slides were air dried, then fixed with 90% acetone and water.

Control antibodies (0.5α, TO/χ, and 1B4) were diluted to a concentration of 1 µg/ml in Phosphate buffered saline, mixed together, and the mixture added to test hybridoma supernatants. Test hybridoma supernatants (35 µl) including the control antibody mixture were then added to separate areas of cells on the slides. Slides were incubated at 37° C. for 30 minutes in a moist chamber. Following incubation, excess solution was aspirated from cells. Slides were washed by soaking for 5 minutes in a slide dish of PBS, with stirring, then air dried.

Second antibody (FITC-conjugated goat anti-human IgG γ chain specific; TAGO, Burlingame, Calif.) was diluted 1:1000 in Evan's blue dye, and 25 µl was added to each cell area. Slides were then incubated at 37° for 30 minutes in a dark, moist chamber. Excess second antibody solution was aspirated and the slides washed in PBS as before, then air dried. Coverslips were mounted onto slides in 90% glycerol, using about 4 µl of mounting medium per cell area. Coverslips were sealed with clear fingernail polish.

Cells were examined under a fluorescence microscope for presence of bound human anti-HTLV-I antibody, as reported by fluorescence labeling.

MO-T Immunofluorescence. Immunofluorescence detection of human anti-HTLV-II antibodies bound to MO-T cells was carried out essentially as described above for MT-2 cells.

Results of immunofluorescence assays are tabulated in Table 1.

D. Live Cell HTLV-I Assay

HTLV-I infected MT-2 cells were grown in a tissue culture flask in RPMI medium supplemented with 10% fetal calf serum. Cells were harvested from the flask and collected by centrifugation at 2000 rpm for 10 minutes in a clinical centrifuge. The cells were suspended in staining medium (PBS +1% fetal calf serum +0.1% Na azide). Cells were centrifuged again, resuspended at $1 \times 10^6$ cells/ 100 µl of staining medium, and aliquoted at a density of $1 \times 10^6$ cells per test tube. Test human monoclonal antibody-containing hybridoma supernatants were added to each test tube (100

μl/tube). Tubes were incubated on ice for 45 minutes, then diluted with 0.8 ml/tube of staining medium, and centrifuged for 10 minutes at 2000 rpm in a clinical centrifuge. Supernatants were aspirated, cells were resuspended in 100 μl staining medium, and FITC-conjugated goat anti-human antibody (1:32 dilution; TAGO) was added to each tube. Incubation was carried out for 45 minutes in an ice bath. One ml of staining solution was then added to each tube, as wash, and tubes were centrifuged at 2000 RPM for 10 minutes, as above. Cells were then resuspended in 1 ml of fixative (formaldehyde) and analyzed for bound fluorescent label by flow cytometry.

EXAMPLE 3

Production of Hybridoma cells

A. Production of Heteromyeloma Fusion Partners

Heteromyeloma cells were produced by fusing EBV activated, IgG-secreting random human lymphocytes (i.e. lymphocytes isolated from non-infected donor) with mouse NS-1 cells. using a polyethylene glycol fusion paradigm well known in the art (Mishell). NS-1 cells are a non-secreting mouse myeloma cell line, such as ATCC TIB18. Fusion of the activated human lymphocytes with NS-1 cells results in a heteromyeloma stable fusion partner cell line, termed H73C11 (Perkins, 1991), provided by J. Larrick, GeneLabs Inc., Redwood City, Calif.

B. Electrofusion of heteromyeloma partner cells with activated lymphocytes.

Cells activated and cultured as described in Example 1 which exhibited anti-HTLV-I activity in the HTLV-I lysate enzyme-based immunoassay (Example 2) were used for production of hybridomas. Approximately $10^5$ EBV activated B cells were combined with $2 \times 10^5$ K6H6-B5 mouse-human heteromyeloma cells. Fusion of about $10^5$ EBV-activated cells with heteromyeloma cells was achieved by electric field induced cell fusion using hypo-osmolar conditions, essentially as described by Perkins (1991) and outlined below.

All steps were performed at room temperature. Electrical current was applied with either the Z1000 Zimmermann Cell Fusion System (GCA) or the Bioject CF (Biomed, Theres, FRG). An approximate range of electrical fusion parameters was first determined by observing the fusion process microscopically in an open fusion chamber. The open chamber consists of two parallel platinum electrodes 200 μm in diameter and 200 μm apart fixed to a glass slide (GCA/Precision Science Group, Chicago, Ill., USA, and chambers made in the mechanical workshop of the Institute of Biotechnology, University of Wurzburg) (Perkins et al., 1987).

Based on results observed in the open chamber, fusions were performed under sterile conditions in helical fusion chambers. These chambers are composed of an electrode assembly containing the same platinum electrodes wound in a helix, and a receptacle to hold the cells (GCA, and made in the mechanical workshop of the Institute of Biotechnology, University of Wurzburg). K6H6 hetermyeloma and EBV-activated cells were pooled, spun and washed once in isoosmolar fusion medium (300 L3) at $10^6$ cells/ml underlayered with an equal volume of 300 L3. Cells were resuspended in hypoosmolar fusion medium and placed in the helical chambers (170- to 250-μl volume, depending on the specific chamber used). After 5–15 minutes in the hypoosmolar medium, electrical current was applied. Cells were first aligned for 30 s in a nonuniform alternating field of 1 MHz 300 V/cm; then direct current of high intensity and short duration (10–15 μs) was applied to promote fusion; and finally the alignment was tapered off gradually over 30 s after fusion. Cells were washed from the chamber 10–15 minutes after fusion, and plated in 96-well microtiter trays in preselection medium containing complete IMDM without pH indicator (Gibco), 15% fetal calf serum, 100 μM hypoxanthine (Sigma, St. Louis, Mo., USA), and 15 μM thymidine (Sigma). Each cell population alone, as well as pooled cells put through the medium changes but not fused, was plated as a control. After 24 hr, the cells were fed selection medium consisting of preselection medium containing phenol red as a pH indicator with the addition of 0.8 μM aminopterin (Sigma) and 0.1 μM ouabain (Sigma). Hybrids were grown for 2 weeks in selection medium, and then returned to preselection medium containing pH indicator.

After no new hybrids appeared in new wells (approximately 5 weeks), the number of wells with growth and the range in colony number/well were determined. The hybridoma formation efficiency is calculated by multiplying the number of wells and colonies and the potential for counting errors. This relative range attempts to incorporate some of the uncertainty and variation inherent in counting large numbers of wells with large numbers of colonies which are not always clearly delineated.

Human hybridomas grew in 57/60 wells with a hybridoma formation efficiency of 114–285 per $10^5$ input B cells. Cultures were tested for anti-HTLV-I activity using the HTLV-I lysate enzyme-based immunoassay (Example 2). One of the wells containing hybridoma growth tested positive for the presence of anti-HTLV-I immunoglobulin in the culture medium. This culture was cloned by limiting dilution to ensure monoclonality (Mishell).

EXAMPLE 4

Production of Recombinant Epitopes

A. Construction of bacterial fusion epitope proteins

Oligonucleotide primers were designed to amplify selected portions of HTLV-I p19 (FIG. 4). Seven such primers were synthesized on an automated DNA synthesizer (Applied Biosystems, Foster City, Calif.), following the manufacturer's instructions. Each of the primers contained an EcoR I site located at its 5' end to facilitate cloning of the amplified DNA molecules. The primers were constructed to facilitate recovery of the open reading frame of the HTLV-I p19 as an in-frame insertion into the pGEX (Pharmacia) expression system (Smith).

The 5' and 3' ends of the HTLV-I DNA sequences of the various HTLV-I p19 recombinant antigens were selected on the basis of the hydrophilicity profiles of HTLV-I p19 as determined by the software package PC-Gene (Intelligenetics, Mountain View, Calif.). Polymerase chain reaction (PCR) was performed according to the manufacturer's instructions (Perkin-Elmer/Cetus). Each PCR reaction contained 2 ng of the HTLV-I clone sp65 MT-2, a full length molecular cline of the Seiki strain of HTLV-I cloned into a plasmid vector pSP65 (provided by Dr F. Wong-Staal, NIH; ProMega, Madison, Wis.) as template and 1.0 μM of the appropriate oligonucleotide primer. PCR amplification was carried out for 25 cycles of template denaturation (1 minute at 94° C.), primer annealing (2 minutes at 50° C.), and primer extension (2 minutes at 72° C.). Amplified DNAs were purified and digested overnight with EcoR I. The digested DNAs were ligated into the EcoR I site of the vector pGEX-2 (Pharmacia), using DNA ligase (Boehringer Mannheim, Indianapolis, Ind.).

Resulting ligated DNA molecules were used to transform competent *E. coli* strain JM-101 (Messing) using standard techniques (Sambrook). Plasmid DNAs from transformed colonies were analyzed for the presence of insert by digestion with either EcoR I (which liberates the cloned insert) and/or Sca I. Sca I cuts the pGEX vectors at 2 sites located 111 basepairs (bp) downstream and 720 bp upstream of the unique EcoR I site and facilitates the identification of clones containing small ($\leq$150 bp) inserts.

Bacteria transformed with an insert-containing plasmid were screened for correct orientation and protein production by Western blot analysis of whole cell lysates prepared from 2 ml cultures of the transformed *E. coli*. Whole cell lysates were prepared as follows: An overnight culture grown in Luria Broth (LB) plus 100 µg/ml ampicillin was diluted 1/10 into 2 mls of fresh LB plus ampicillin and grown for 1 hour at 37° C. Expression of recombinant fusion protein was induced by addition of 5 µl of 0.1 M isopropyl thiogalactoside (IPTG) to each culture. The cells were grown at 37° C. for an additional 3–4 hours at which time 2 ml aliquots of the cultures were pelleted by centrifugation in a microfuge. The pelleted cells were resuspended in 100 µl of MTBS (150 mM NaCl, 20 mM Sodium Phosphate, pH 8.0), to which was added 100 µl of 2× SB (10% β-mercaptoethanol, 20% glycerol, 4.6% sodium dodecyl sulfate (SDS), and 125 mM Tris-HCl pH 6.8). Samples were boiled for 5 minutes and debris pelleted by centrifugation for 5 minutes in a microfuge. Aliquots of the boiled samples were subsequently fractionated by sodium dodecyl sulfate Polyacrylamide Gel electrophoreses (SDS-PAGE, 23) using 12% acrylamide gels. The fractionated proteins were either stained with Coomassie blue or blotted onto nitrocellulose filter paper (Schleicher and Schuell) for Western blotting. Western blots were screened with the IH-9 HMAb and/or a variety of antisera from HTLV-I infected and uninfected individuals. The production of recombinant proteins containing non-immunogenic regions of HTLV-I p19 was confirmed through the use of a rabbit antisera containing antibodies directed against non-recombinant glutathione S-transferase (produced in New Zealand White Rabbits using glutathione S-transferase as antigen; Joslyn Laboratories, Santa Rosa, Calif.).

B. Purification of recombinant fusion protein antigen epitopes

Purification of recombinant fusion protein was performed essentially as described by Smith. Briefly, a 10 ml overnight culture of bacteria containing the recombinant plasmid of interest was diluted 1/100 into flasks containing 500 mls NZYDT media (Sambrook) containing 100 $\mu$g/ml ampicillin. The cultures were grown until absorbance at 600 nm measured on the undiluted supernatant was approximately 0.5. Production of fusion protein was induced by addition of isopropyl thiogalactosidase (IPTG) to a final concentration of 0.2 mM. The cultures were incubated for an additional 3 to 4 hours, then the bacteria were pelleted by centrifugation at 5000× g for 10 minutes. Bacterial cells were resuspended in 20 milliliters cold isotonic buffer (MTBS) for each liter of culture. The bacteria were lysed by 2 passes through a French Press (Amicon) at a gauge pressure of 1200. After lysis, proteins were solubilized by the addition of Triton-X100 (Sigma) to a final concentration of 1.0%. Sufficient DNAse I, and aprotinin were also added at this time to achieve final concentrations of 1 $\mu$g/ml and 1.0%, respectivly. The supernatant fraction was then incubated for 5 minutes at 25° C., and insoluble cellular debris was pelleted by centrifugation two times at 10,000× g for 10 minutes. The supernatant was reserved, and the pellet was resuspended in 20 mls of MTBS for each liter of original culture. Aliquots from both the pellet and supernatant fractions were analyzed by SDS-PAGE to determine if the recombinant proteins were solubilized by the above procedure. Significant amounts of the recombinant protein pR45 were found in the supernant fraction. The supernatant was then passed through a column containing 0.8 ml of glutathione agarose (Pharmacia), which was pre-treated as recommended by the manufacturer. The column was washed with 10 ml of MTBS containing 1% Triton and 1% aprotinin. This was followed by a 3 ml wash with MTBS alone. Bound proteins were eluted with buffer containing 5 mM glutathione in 50 mM Tris pH 8.0. Ten fractions (approximately 1 ml each) were collected. The location of the peak of eluted protein was determined by measuring absorbance at 280 nm of each fraction. Additionally, SDS-PAGE analysis was carried out on aliquots of each fraction. Fractions containing significant amounts of protein were pooled, and aliquots of this pool were frozen at −70° C. for subsequent analysis.

EXAMPLE 5

Localization of IH-9 human Monoclonal Antibody-specific Antigen Epitope

Six recombinant clones containing various portions of HTLV-I p19 expressed as fusion proteins with glutathione S-trnaferase were constructed using methods described in Example 4. Whole cell lysates from bacteria transformed with each of the 6 HTLV-I p19 recombinant proteins were prepared as described in Example 4 and fractionated by SDS PAGE. The resulting gels were blotted onto nitrocellulose overnight using a Hoefer Transphor unit (Hoefer Scientific Instruments, San Francisco, Calif.). The resulting nitrocellulose blots were blocked by a 4 hour incubation in BLOTTO (10 mM TRIS-HCl, pH 7.5, 0.05% Tween-20). The Western blots were then incubated overnight at 25° C. with supernatant from an active culture of the IH-9 secreting cells diluted 1:2 in BLOTTO. The Western blots were removed from the IH-9 supernatant and washed three times at 25° for 5 minutes each. The blots were incubated for one hour at 25° with alkaline phosphatase conjugated goat-anti-human IgG (ProMega) diluted 1/7500 in BLOTTO. This was followed by another set of four 5 minute substrate washes with Tris buffered saline. Bound second antibody was detected by incubating the stirps in a substrate solution containing 5-bromo-4-chloro 3-indolylphosphate (BCIP) and Nitroblue tetrazolium (NBT) in 100 mM Tris-HCl, pH9.5 and 50 mM $MgCl_2$. The recombinant fusion protein antigens p19-R45 and p19-LB27 were clearly identified by the IH-9 monoclonal antibody supernatant (FIG. 6). Faint immunoreactivity of the IH-9 HMAb toward the full length HTLV-I p19 recombinant p19-FL130 was also observed (lane c). NO immunoreactivity toward any of the other HTLV-I p19 recombinant proteins was observed.

While the invention has been described with reference to specific methods and embodiments, it will be appreciated that various modifications and changes may be made without departing from the invention.

It is claimed:

1. A kit for positively identifying HTLV-I infection in a human serum sample, comprising
   a device having a solid support on which is immobilized
   (a) an HTLV-I p19 peptide antigen consisting of the amino acid sequence presented as SEQ ID NO: 1, and
   (b) an HTLV-I gp46 peptide antigen consisting of the amino acid sequence presented as SEQ ID NO: 4, and which is specifically immunoreactive with sera from individuals infected with HTLV-I, but is not specifically immunoreactive with sera from individuals infected with HTLV-II, and
   means for detecting the presence of human antibodies bound immunospecifically to each of the peptide antigens attached to the solid support.

2. The kit of claim 1, wherein the p19 and gp46 peptide antigens are carried on separate regions of a solid support.

3. The kit of claim 1, wherein said detecting means includes
   (a) an HTLV-I p19 peptide antigen consisting of the amino acid sequence presented as SEQ ID NO: 1, and labeled with a detectable reporter, and
   (b) an HTLV-I gp46 peptide antigen consisting of the amino acid sequence presented as SEQ ID NO: 4, and which is specifically immunoreactive with sera from individuals infected with HTLV-I, but is not specifically immunoreactive with sera from individuals infected with HTLV-II, and labeled with a detectable reporter.

4. The kit of claim 3, wherein the immobilized p19 and gp46 peptide antigens are attached to the same region of the solid support, and the reporter in the labeled p19 peptide antigen can be distinguished from the reporter in the labeled gp46 peptide antigen.

5. A kit for use in positively identifying HTLV-I and HTLV-II infection in a human serum sample, comprising
   a device having a solid support on which are immobilized a group of antigens consisting of
   (a) an HTLV-I p19 peptide antigen consisting of the amino acid sequence presented as SEQ ID NO: 1,
   (b) an HTLV-I gp46 peptide antigen consisting of the amino acid sequence presented as SEQ ID NO: 4, and which is specifically immunoreactive with sera from individuals infected with HTLV-I, but is not specifically immunoreactive with sera from individuals infected with HTLV-II,
   (c) an HTLV-II p21 peptide antigen consisting of the amino acid sequence presented as SEQ ID NO: 3, and
   (d) a peptide antigen consisting of the amino acid sequence presented as SEQ ID NO:5, and which is specifically immunoreactive with sera from individuals infected with HTLV-II, but not specifically immunoreactive with sera from individuals infected with HTLV-I, and
   detecting means effective for detecting the presence of human antibodies bound immunospecifically to each of the peptide antigens (a)–(d) immobilized on the solid support.

6. The kit of claim 5, wherein said detecting means further includes (c) an HTLV-II p21 peptide antigen consisting of the amino acid sequence presented as SEQ ID NO: 3, and labeled with a detectable reporter, and (d) a peptide antigen consisting of the amino acid sequence presented as SEQ ID NO:5, and which is specifically immunoreactive with sera from individuals infected with HTLV-II, but is not specifically immunoreactive with sera from individuals infected with HTLV-I, and labeled with a detectable reporter.

7. A kit for positively identifying HTLV-II infection in a human serum sample, comprising
   a solid support on which are immobilized (a) an HTLV-II peptide antigen consisting of the epitope formed by the amino acid sequence SEQ ID NO: 3, and (b) an HTLV-II peptide antigen consisting of the epitope formed by the amino acid sequence SEQ ID NO: 5, and
   means for detecting the presence of human antibodies bound immunospecifically to each of the peptide antigens attached to the solid support.

8. The kit of claim 7, wherein the two HTLV-II peptide antigens are carried on separate regions of a solid support.

9. The kit of claim 7, wherein said detecting means includes (a) an HTLV-II peptide antigen consisting of the epitope formed by the amino acid sequence SEQ ID NO: 3, and labeled with a detectable reporter, and (b) an HTLV-II antigen consisting of the epitope formed by the amino acid sequence SEQ ID NO: 5 and labeled with a detectable reporter.

10. The kit of claim 9 wherein the two peptide antigens are attached to the same region of the solid support, and the reporter in one of the labeled peptide antigens can be distinguished from the reporter in the other labeled peptide antigen.

11. An immunoreactive peptide antigen derived from HTLV II gp46, consisting of the sequence presented as SEQ ID NO:5.

12. A method for positively identifying HTLV-I infection in a human serum sample, comprising
   reacting the serum sample with a device having a solid support on which are immobilized a group of antigens consisting of
   (a) an HTLV-I p19 peptide antigen consisting of the amino acid sequence presented as SEQ ID NO: 1,
   (b) an HTLV-I gp46 peptide antigen consisting of the amino acid sequence presented as SEQ ID NO: 4, and which is specifically immunoreactive with sera from individuals infected with HTLV-I, but not specifically immunoreactive with sera from individuals infected with HTLV-II, detecting the binding of human serum antibodies to each of said peptide antigens (a) and (b) separately, and making a positive identification of HTLV-I infection if and only if the binding of serum-antibodies to both peptide antigens is observed.

13. The method of claim 12, wherein said detecting includes contacting the solid support and human serum antibodies bound thereto with (a) an HTLV-I p19 peptide antigen consisting of the amino acid sequence presented as SEQ ID NO: 1, (b) an HTLV-I gp46 peptide antigen consisting of the amino acid sequence presented as SEQ ID NO: 4, and which is specifically immunoreactive with sera from individuals infected with HTLV-I, but is not specifically immunoreactive with sera from individuals infected with HTLV-II, and labeled with a detectable reporter, to bind the labeled peptide antigens to the solid support, washing the support to remove non-specifically bound labeled peptides, and detecting the presence of said labeled reporters bound to the solid support.

14. The method of claim 13, wherein the immobilized p19 and gp46 peptide antigens are attached to the same region of the solid support, and the reporter in the labeled p19 peptide antigen can be distinguished from the reporter in the labeled gp46 peptide antigen.

15. A method for use in positively identifying HTLV-I and HTLV-II infection in a human serum sample, comprising reacting the serum sample with a device having a solid support on which are immobilized a group of antigens consisting of (a) an HTLV-I p19 peptide antigen consisting of the amino acid sequence presented as SEQ ID NO: 1, (b) an HTLV-I gp46 peptide antigen consisting of the amino acid sequence presented as SEQ ID NO: 4, and which is specifically immunoreactive with sera from individuals infected with HTLV-I, but is not specifically immunoreactive with sera from individuals infected with HTLV-II, (c) an HTLV-II p21 peptide antigen consisting of the amino acid sequence presented as SEQ ID NO: 3, and (d) a peptide antigen consisting of the amino acid sequence presented as SEQ ID NO:5, and which is specifically immunoreactive with sera from individuals infected with HTLV-II, but not specifically immunoreactive with sera from individuals infected with HTLV-I, detecting the presence of human antibodies bound immunospecifically to each of said peptide antigens (a)–(d) immobilized on the support, and making a positive identification of HTLV-I infection if and only if the binding of serum antibodies to both peptides (a) and (b) is observed, and making a positive identification of HTLV-II infection if and only if the binding of serum antibodies to both peptides (c) and (d) is observed.

* * * * *

UNITED STATES PATENT AND TRADEMARK OFFICE
CERTIFICATE OF CORRECTION

PATENT NO : 6,110,662
DATED : August 29, 2000
INVENTOR(S): Foung et al.

It is certified that error appears in the above-identified patent and that said Letters Patent are hereby corrected as shown below:

Column 1, line 5, insert

This invention was made with Government support under contracts AI22557 and HL33811 awarded by the National Institutes of Health. The Government has certain rights in this invention.

Signed and Sealed this

Fifteenth Day of May, 2001

Attest:

NICHOLAS P. GODICI

Attesting Officer

Acting Director of the United States Patent and Trademark Office

UNITED STATES PATENT AND TRADEMARK OFFICE
CERTIFICATE OF CORRECTION

PATENT NO. : 6,110,662  
DATED : August 29, 2000  
INVENTOR(S) : Foung et al.

Page 1 of 1

It is certified that error appears in the above-identified patent and that said Letters Patent is hereby corrected as shown below:

Column 1:  
Line 5, insert:

This invention was made with Government support under contracts HL33811 and DA06596 awarded by the National Institutes of Health. The Government has certain rights in this invention.

Signed and Sealed this

Twenty-sixth Day of June, 2001

Attest:

NICHOLAS P. GODICI  
Attesting Officer    Acting Director of the United States Patent and Trademark Office